(12) United States Patent
Mori

(10) Patent No.: US 7,585,938 B2
(45) Date of Patent: Sep. 8, 2009

(54) GAMMA-SECRETASE INHIBITORS

(76) Inventor: Hiroshi Mori, 3-45-301, Nakamachi 1-chome, Higashinari-ku, Osaka-shi, Osaka (JP) 537-0025

( * ) Notice: Subject to any disclaimer, the term of this patent is extended or adjusted under 35 U.S.C. 154(b) by 591 days.

(21) Appl. No.: 10/511,269

(22) PCT Filed: Apr. 18, 2003

(86) PCT No.: PCT/JP03/05017

§ 371 (c)(1),
(2), (4) Date: Oct. 20, 2004

(87) PCT Pub. No.: WO03/091278

PCT Pub. Date: Nov. 6, 2003

(65) Prior Publication Data

US 2006/0205666 A1  Sep. 14, 2006

(30) Foreign Application Priority Data

Apr. 24, 2002 (JP) ............................. 2002-121983

(51) Int. Cl.
*A61K 38/10* (2006.01)
(52) U.S. Cl. ........................................ 530/326; 514/14
(58) Field of Classification Search ....................... None
See application file for complete search history.

(56) References Cited

U.S. PATENT DOCUMENTS

2002/0013276 A1  1/2002  Nadin et al.

FOREIGN PATENT DOCUMENTS

EP          236734       9/1987
WO    WO 01/53255 A1    7/2001

OTHER PUBLICATIONS

AX- Yu et al., J. of Bio. Chem., 2001, vol. 276, No. 47, pp. 43756-43760.*
Konvalinka et al., Eur. J. Biochem., 1997, vol. 250, pp. 559-566.*
Magdalena Sastre, et al., "Presenilin-dependent γ-secretase processing of β-amyloid precursor protein at a site corresponding to the S3 cleavage of Notch", EMBO reports, vol. 2, No. 9, XP-002373229, Sep. 2001, pp. 835-841.
Chunjiang Yu, et al., "Characterization of a Presenilin-mediated Amyloid Precursor Protein Carboxyl-terminal Fragment γ Evidence for Distinct Mechanisms Involved in γ-Secretase Processing of the APP and Notch 1 Transmembrane Domains", vol. 276, No. 47, XP-002373230, Nov. 23, 2001, pp. 43756-43760.

Gu Y. et al., Distinct intramembrane cleavage of the beta-amyloid precursor protein family resembling gamma-secretase-like cleavage of Notch. J.Biol.Chem., vol. 276, No. 38, p. 35235-8, Sep. 21, 2001.
Shearman M.S. et al., L-685, 458, an aspartyl protease transition state mimic, is a potent inhibitor of amyloid beta-protein precursor gamma-secretase activity. Biochemistry, vol. 39, No. 30, p. 8698-704, Aug. 1, 2000.
Wolfe M.S. et al., A substrate-based difluoro ketone selectively inhibits Alzheimer's gamma-secretase activity. J.Med.Chem., vol. 41 No. 1. pp. 6 to 9, Jan. 1, 1998.
Schwarze, Steven R. et al., In vivo protein transduction: delivery of a biologically active protein into the mouse. Science vol. 285, pp. 1569 to 1572, Sep. 3, 1999.
Weidemann A. et al., A novel epsilon-cleavage within the transmembrane domain of the Alzheimer amyloid precursor protein demonstrates homology with Notch processing. Biochemistry, vol. 41 No. 8, p. 2825-35, Feb. 26, 2002.
Pinnix I., et al., A novel gamma-secretase assay based on detection of the putative C-terminal fragment-gamma of amyloid beta protein precursor. J.Biol.Chem., vol. 276 No. 1, p. 481-7, Jan. 5, 2001.
Figueiredo-Pereira M.E. et al., Distinct secretases, a cysteine protease and a serine protease, generate the C termini of amyloid beta-proteins Abetal-40 and Abetal-42, respectively. J.Neurochem., vol. 72 No. 4, p. 1417-22, Apr. 1999.
Ghosh A.K. et al., Structure-based design: potent inhibitors of human brain memapsin 2. (.beta.-secretase). Journal of Medicinal Chemistry, vol. 44 No. 18, pp. 2865 to 2868, 2001.
Chong K.T. et al., Peptidomimetic HIV protease inhibitors: phosphate prodrugs with improved biological activities. Journal of Medicinal Chemistry, vol. 36 No. 17, p. 2575-7, 1993.
Tian G. et al., Linear non-competitive inhibition of solubilized human gamma-secretase by pepstatin A methylaster, L685458, sulfonamides, and benzodiazepines. J.Biol.Chem., vol. 277 No. 35, p. 31499-505, Aug. 30, 2002.

* cited by examiner

Primary Examiner—Christopher R. Tate
Assistant Examiner—Roy Teller
(74) Attorney, Agent, or Firm—Oblon, Spivak, McClelland, Maier & Neustadt, P.C.

(57) ABSTRACT

Disclosed, as a γ-secretase inhibitor, is a compound consisting of an amino acid sequence which consists of at least three consecutive amino acids of the amino acid sequence Val-Val-Ile-Ala-Thr-Val-Ile-Val-Ile-Thr-Leu-Val-Met-Leu-Lys-Lys-Lys including Leu at position 11, wherein, between the Leu and one or both amino acids located immediately before or after it, the peptide bond, —CO—NH—, is replaced with a hydroxyethylene group, —CHOH—CH$_2$—, wherein the N terminus has an alkyloxycarbonyl group based on C1-10 alkyl that may carry phenyl or naphthyl as a substituent group, wherein the C terminus is converted to alkyl ester or alkyl amide based on C1-10 alkyl that may carry phenyl or naphthyl as a substituent group, and wherein the hydrogen atom of the hydroxyl group of the Thr at position 10 may be replaced with a C1-4 hydrophobic group or a Z group, or a pharmaceutically acceptable salt thereof.

2 Claims, 6 Drawing Sheets

SEQUENCE LISTING

<160> NUMBER OF SEQ ID NOS: 13

<210> SEQ ID NO 1
<211> LENGTH: 17
<212> TYPE: PRT
<213> ORGANISM: Homo sapiens

<400> SEQUENCE: 1

Val Val Ile Ala Thr Val Ile Val Ile Thr Leu Val Met Leu Lys Lys
1               5                   10                  15

Lys

<210> SEQ ID NO 2
<211> LENGTH: 6
<212> TYPE: PRT
<213> ORGANISM: Homo sapiens

<400> SEQUENCE: 2

Ile Thr Leu Val Met Leu
1               5

<210> SEQ ID NO 3
<211> LENGTH: 4
<212> TYPE: PRT
<213> ORGANISM: Homo sapiens

<400> SEQUENCE: 3

Leu Val Met Leu
1

<210> SEQ ID NO 4
<211> LENGTH: 4
<212> TYPE: PRT
<213> ORGANISM: Homo sapiens

<400> SEQUENCE: 4

Thr Leu Val Met
1

<210> SEQ ID NO 5
<211> LENGTH: 11
<212> TYPE: PRT
<213> ORGANISM: Homo sapiens

<400> SEQUENCE: 5

Tyr Gly Arg Lys Lys Arg Arg Gln Arg Arg Arg
1               5                   10

<210> SEQ ID NO 6
<211> LENGTH: 2088
<212> TYPE: DNA
<213> ORGANISM: Homo sapiens
<220> FEATURE:
<221> NAME/KEY: CDS
<222> LOCATION: (1)..(2088)

<400> SEQUENCE: 6

```
atg ctg ccc ggt ttg gca ctg ctc ctg ctg gcc gcc tgg acg gct cgg     48
Met Leu Pro Gly Leu Ala Leu Leu Leu Leu Ala Ala Trp Thr Ala Arg
1               5                   10                  15 gcg ctg gag gta ccc act gat ggt aat gct ggc ctg ctg gct gaa ccc     96
Ala Leu Glu Val Pro Thr Asp Gly Asn Ala Gly Leu Leu Ala Glu Pro
                20                  25                  30
```

```
cag att gcc atg ttc tgt ggc aga ctg aac atg cac atg aat gtc cag      144
Gln Ile Ala Met Phe Cys Gly Arg Leu Asn Met His Met Asn Val Gln
    35                  40                  45 aat ggg aag tgg gat tca gat cca tca ggg acc aaa acc tgc att gat      192
Asn Gly Lys Trp Asp Ser Asp Pro Ser Gly Thr Lys Thr Cys Ile Asp
 50                  55                  60 acc aag gaa ggc atc ctg cag tat tgc caa gaa gtc tac cct gaa ctg      240
Thr Lys Glu Gly Ile Leu Gln Tyr Cys Gln Glu Val Tyr Pro Glu Leu
 65                  70                  75                  80 cag atc acc aat gtg gta gaa gcc aac caa cca gtg acc atc cag aac      288
Gln Ile Thr Asn Val Val Glu Ala Asn Gln Pro Val Thr Ile Gln Asn
                 85                  90                  95 tgg tgc aag cgg ggc cgc aag cag tgc aag acc cat ccc cac ttt gtg      336
Trp Cys Lys Arg Gly Arg Lys Gln Cys Lys Thr His Pro His Phe Val
            100                 105                 110 att ccc tac cgc tgc tta gtt ggt gag ttt gta agt gat gcc ctt ctc      384
Ile Pro Tyr Arg Cys Leu Val Gly Glu Phe Val Ser Asp Ala Leu Leu
        115                 120                 125 gtt cct gac aag tgc aaa ttc tta cac cag gag agg atg gat gtt tgc      432
Val Pro Asp Lys Cys Lys Phe Leu His Gln Glu Arg Met Asp Val Cys
130                 135                 140 gaa act cat ctt cac tgg cac acc gtc gcc aaa gag aca tgc agt gag      480
Glu Thr His Leu His Trp His Thr Val Ala Lys Glu Thr Cys Ser Glu
145                 150                 155                 160 aag agt acc aac ttg cat gac tac ggc atg ttg ctg ccc tgc gga att      528
Lys Ser Thr Asn Leu His Asp Tyr Gly Met Leu Leu Pro Cys Gly Ile
                165                 170                 175 gac aag ttc cga ggg gta gag ttt gtg tgt tgc cca ctg gct gaa gaa      576
Asp Lys Phe Arg Gly Val Glu Phe Val Cys Cys Pro Leu Ala Glu Glu
            180                 185                 190 agt gac aat gtg gat tct gct gat gcg gag gag gat gac tcg gat gtc      624
Ser Asp Asn Val Asp Ser Ala Asp Ala Glu Glu Asp Asp Ser Asp Val
        195                 200                 205 tgg tgg ggc gga gca gac aca gac tat gca gat ggg agt gaa gac aaa      672
Trp Trp Gly Gly Ala Asp Thr Asp Tyr Ala Asp Gly Ser Glu Asp Lys
210                 215                 220 gta gta gaa gta gca gag gag gaa gtg gct gag gtg gaa gaa gaa          720
Val Val Glu Val Ala Glu Glu Glu Val Ala Glu Val Glu Glu Glu
225                 230                 235                 240 gaa gcc gat gat gac gag gac gat gag gat ggt gat gag gta gag gaa      768
Glu Ala Asp Asp Asp Glu Asp Asp Glu Asp Gly Asp Glu Val Glu Glu
                245                 250                 255 gag gct gag gaa ccc tac gaa gaa gcc aca gag aga acc acc agc att      816
Glu Ala Glu Glu Pro Tyr Glu Glu Ala Thr Glu Arg Thr Thr Ser Ile
            260                 265                 270 gcc acc acc acc acc acc aca gag tct gtg gaa gag gtg gtt cga          864
Ala Thr Thr Thr Thr Thr Thr Glu Ser Val Glu Glu Val Val Arg
        275                 280                 285 gtt cct aca aca gca gcc agt acc cct gat gcc gtt gac aag tat ctc      912
Val Pro Thr Thr Ala Ala Ser Thr Pro Asp Ala Val Asp Lys Tyr Leu
        290                 295                 300 gag aca cct ggg gat gag aat gaa cat gcc cat ttc cag aaa gcc aaa      960
Glu Thr Pro Gly Asp Glu Asn Glu His Ala His Phe Gln Lys Ala Lys
305                 310                 315                 320 gag agg ctt gag gcc aag cac cga gag aga atg tcc cag gtc atg aga      1008
Glu Arg Leu Glu Ala Lys His Arg Glu Arg Met Ser Gln Val Met Arg
                325                 330                 335
```

```
gaa tgg gaa gag gca gaa cgt caa gca aag aac ttg cct aaa gct gat    1056
Glu Trp Glu Glu Ala Glu Arg Gln Ala Lys Asn Leu Pro Lys Ala Asp
        340                 345                 350 aag aag gca gtt atc cag cat ttc cag gag aaa gtg gaa tct ttg gaa    1104
Lys Lys Ala Val Ile Gln His Phe Gln Glu Lys Val Glu Ser Leu Glu
        355                 360                 365 cag gaa gca gcc aac gag aga cag cag ctg gtg gag aca cac atg gcc    1152
Gln Glu Ala Ala Asn Glu Arg Gln Gln Leu Val Glu Thr His Met Ala
    370                 375                 380 aga gtg gaa gcc atg ctc aat gac cgc cgc cgc ctg gcc ctg gag aac    1200
Arg Val Glu Ala Met Leu Asn Asp Arg Arg Arg Leu Ala Leu Glu Asn
385                 390                 395                 400 tac atc acc gct ctg cag gct gtt cct cct cgg cct cgt cac gtg ttc    1248
Tyr Ile Thr Ala Leu Gln Ala Val Pro Pro Arg Pro Arg His Val Phe
                405                 410                 415 aat atg cta aag aag tat gtc cgc gca gaa cag aag gac aga cag cac    1296
Asn Met Leu Lys Lys Tyr Val Arg Ala Glu Gln Lys Asp Arg Gln His
            420                 425                 430 acc cta aag cat ttc gag cat gtg cgc atg gtg gat ccc aag aaa gcc    1344
Thr Leu Lys His Phe Glu His Val Arg Met Val Asp Pro Lys Lys Ala
        435                 440                 445 gct cag atc cgg tcc cag gtt atg aca cac ctc cgt gtg att tat gag    1392
Ala Gln Ile Arg Ser Gln Val Met Thr His Leu Arg Val Ile Tyr Glu
    450                 455                 460 cgc atg aat cag tct ctc tcc ctg ctc tac aac gtg cct gca gtg gcc    1440
Arg Met Asn Gln Ser Leu Ser Leu Leu Tyr Asn Val Pro Ala Val Ala
465                 470                 475                 480 gag gag att cag gat gaa gtt gat gag ctg ctt cag aaa gag caa aac    1488
Glu Glu Ile Gln Asp Glu Val Asp Glu Leu Leu Gln Lys Glu Gln Asn
                485                 490                 495 tat tca gat gac gtc ttg gcc aac atg att agt gaa cca agg atc agt    1536
Tyr Ser Asp Asp Val Leu Ala Asn Met Ile Ser Glu Pro Arg Ile Ser
            500                 505                 510 tac gga aac gat gct ctc atg cca tct ttg acc gaa acg aaa acc acc    1584
Tyr Gly Asn Asp Ala Leu Met Pro Ser Leu Thr Glu Thr Lys Thr Thr
        515                 520                 525 gtg gag ctc ctt ccc gtg aat gga gag ttc agc ctg gac gat ctc cag    1632
Val Glu Leu Leu Pro Val Asn Gly Glu Phe Ser Leu Asp Asp Leu Gln
    530                 535                 540 ccg tgg cat tct ttt ggg gct gac tct gtg cca gcc aac aca gaa aac    1680
Pro Trp His Ser Phe Gly Ala Asp Ser Val Pro Ala Asn Thr Glu Asn
545                 550                 555                 560 gaa gtt gag cct gtt gat gcc cgc cct gct gcc gac cga gga ctg acc    1728
Glu Val Glu Pro Val Asp Ala Arg Pro Ala Ala Asp Arg Gly Leu Thr
                565                 570                 575 act cga cca ggt tct ggg ttg aca aat atc aag acg gag gag atc tct    1776
Thr Arg Pro Gly Ser Gly Leu Thr Asn Ile Lys Thr Glu Glu Ile Ser
            580                 585                 590 gaa gtg aag atg gat gca gaa ttc cga cat gac tca gga tat gaa gtt    1824
Glu Val Lys Met Asp Ala Glu Phe Arg His Asp Ser Gly Tyr Glu Val
        595                 600                 605 cat cat caa aaa ttg gtg ttc ttt gca gaa gat gtg ggt tca aac aaa    1872
His His Gln Lys Leu Val Phe Phe Ala Glu Asp Val Gly Ser Asn Lys
    610                 615                 620 ggt gca atc att gga ctc atg gtg ggc ggt gtt gtc ata gcg aca gtg    1920
Gly Ala Ile Ile Gly Leu Met Val Gly Gly Val Val Ile Ala Thr Val
625                 630                 635                 640 atc gtc atc acc ttg gtg atg ctg aag aag aaa cag tac aca tcc att    1968
Ile Val Ile Thr Leu Val Met Leu Lys Lys Lys Gln Tyr Thr Ser Ile
                645                 650                 655
```

```
cat cat ggt gtg gtg gag gtt gac gcc gct gtc acc cca gag gag cgc    2016
His His Gly Val Val Glu Val Asp Ala Ala Val Thr Pro Glu Glu Arg
        660                 665                 670 cac ctg tcc aag atg cag cag aac ggc tac gaa aat cca acc tac aag    2064
His Leu Ser Lys Met Gln Gln Asn Gly Tyr Glu Asn Pro Thr Tyr Lys
        675                 680                 685 ttc ttt gag cag atg cag aac tag                                    2088
Phe Phe Glu Gln Met Gln Asn
        690             695

<210> SEQ ID NO 7
<211> LENGTH: 695
<212> TYPE: PRT
<213> ORGANISM: Homo sapiens

<400> SEQUENCE: 7

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
            85                  90                  95

Trp Cys Lys Arg Gly Arg Lys Gln Cys Lys Thr His Pro His Phe Val
        100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
    290                 295                 300
```

```
Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
            325                 330                 335

Glu Trp Glu Glu Ala Glu Arg Gln Ala Lys Asn Leu Pro Lys Ala Asp
        340                 345                 350

Lys Lys Ala Val Ile Gln His Phe Gln Glu Lys Val Glu Ser Leu Glu
    355                 360                 365

Gln Glu Ala Ala Asn Glu Arg Gln Gln Leu Val Glu Thr His Met Ala
370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Lys Met Asp Ala Glu Phe Arg His Asp Ser Gly Tyr Glu Val
        595                 600                 605

His His Gln Lys Leu Val Phe Phe Ala Glu Asp Val Gly Ser Asn Lys
610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
        675                 680                 685

Phe Phe Glu Gln Met Gln Asn
690                 695

<210> SEQ ID NO 8
<211> LENGTH: 2313
<212> TYPE: DNA
```

<213> ORGANISM: Homo sapiens
<220> FEATURE:
<221> NAME/KEY: CDS
<222> LOCATION: (1)..(2313)

<400> SEQUENCE: 8

```
atg ctg ccc ggt ttg gca ctg ctc ctg gcc gcc tgg acg gct cgg        48
Met Leu Pro Gly Leu Ala Leu Leu Leu Ala Ala Trp Thr Ala Arg
 1               5                  10                  15 gcg ctg gag gta ccc act gat ggt aat gct ggc ctg ctg gct gaa ccc    96
Ala Leu Glu Val Pro Thr Asp Gly Asn Ala Gly Leu Leu Ala Glu Pro
                 20                  25                  30 cag att gcc atg ttc tgt ggc aga ctg aac atg cac atg aat gtc cag    144
Gln Ile Ala Met Phe Cys Gly Arg Leu Asn Met His Met Asn Val Gln
             35                  40                  45 aat ggg aag tgg gat tca gat cca tca ggg acc aaa acc tgc att gat    192
Asn Gly Lys Trp Asp Ser Asp Pro Ser Gly Thr Lys Thr Cys Ile Asp
         50                  55                  60 acc aag gaa ggc atc ctg cag tat tgc caa gaa gtc tac cct gaa ctg    240
Thr Lys Glu Gly Ile Leu Gln Tyr Cys Gln Glu Val Tyr Pro Glu Leu
 65                  70                  75                  80 cag atc acc aat gtg gta gaa gcc aac caa cca gtg acc atc cag aac    288
Gln Ile Thr Asn Val Val Glu Ala Asn Gln Pro Val Thr Ile Gln Asn
                 85                  90                  95 tgg tgc aag cgg ggc cgc aag cag tgc aag acc cat ccc cac ttt gtg    336
Trp Cys Lys Arg Gly Arg Lys Gln Cys Lys Thr His Pro His Phe Val
                100                 105                 110 att ccc tac cgc tgc tta gtt ggt gag ttt gta agt gat gcc ctt ctc    384
Ile Pro Tyr Arg Cys Leu Val Gly Glu Phe Val Ser Asp Ala Leu Leu
            115                 120                 125 gtt cct gac aag tgc aaa ttc tta cac cag gag agg atg gat gtt tgc    432
Val Pro Asp Lys Cys Lys Phe Leu His Gln Glu Arg Met Asp Val Cys
        130                 135                 140 gaa act cat ctt cac tgg cac acc gtc gcc aaa gag aca tgc agt gag    480
Glu Thr His Leu His Trp His Thr Val Ala Lys Glu Thr Cys Ser Glu
145                 150                 155                 160 aag agt acc aac ttg cat gac tac ggc atg ttg ctg ccc tgc gga att    528
Lys Ser Thr Asn Leu His Asp Tyr Gly Met Leu Leu Pro Cys Gly Ile
                165                 170                 175 gac aag ttc cga ggg gta gag ttt gtg tgt tgc cca ctg gct gaa gaa    576
Asp Lys Phe Arg Gly Val Glu Phe Val Cys Cys Pro Leu Ala Glu Glu
            180                 185                 190 agt gac aat gtg gat tct gct gat gcg gag gag gat gac tcg gat gtc    624
Ser Asp Asn Val Asp Ser Ala Asp Ala Glu Glu Asp Asp Ser Asp Val
        195                 200                 205 tgg tgg ggc gga gca gac aca gac tat gca gat ggg agt gaa gac aaa    672
Trp Trp Gly Gly Ala Asp Thr Asp Tyr Ala Asp Gly Ser Glu Asp Lys
    210                 215                 220 gta gta gaa gta gca gag gag gaa gtg gct gag gtg gaa gaa gaa        720
Val Val Glu Val Ala Glu Glu Glu Val Ala Glu Val Glu Glu Glu
225                 230                 235                 240 gaa gcc gat gat gac gag gac gat gag gat ggt gat gag gta gag gaa    768
Glu Ala Asp Asp Asp Glu Asp Asp Glu Asp Gly Asp Glu Val Glu Glu
                245                 250                 255 gag gct gag gaa ccc tac gaa gaa gcc aca gag aga acc acc agc att    816
Glu Ala Glu Glu Pro Tyr Glu Glu Ala Thr Glu Arg Thr Thr Ser Ile
            260                 265                 270 gcc acc acc acc acc acc aca gag tct gtg gaa gag gtg gtt cga        864
Ala Thr Thr Thr Thr Thr Thr Glu Ser Val Glu Glu Val Val Arg
        275                 280                 285
```

```
                                                          -continued gag gtg tgc tct gaa caa gcc gag acg ggg ccg tgc cga gca atg atc    912
Glu Val Cys Ser Glu Gln Ala Glu Thr Gly Pro Cys Arg Ala Met Ile
    290             295                 300 tcc cgc tgg tac ttt gat gtg act gaa ggg aag tgt gcc cca ttc ttt    960
Ser Arg Trp Tyr Phe Asp Val Thr Glu Gly Lys Cys Ala Pro Phe Phe
305                 310                 315                 320 tac ggc gga tgt ggc ggc aac cgg aac aac ttt gac aca gaa gag tac   1008
Tyr Gly Gly Cys Gly Gly Asn Arg Asn Asn Phe Asp Thr Glu Glu Tyr
                325                 330                 335 tgc atg gcc gtg tgt ggc agc gcc atg tcc caa agt tta ctc aag act   1056
Cys Met Ala Val Cys Gly Ser Ala Met Ser Gln Ser Leu Leu Lys Thr
            340                 345                 350 acc cag gaa cct ctt ggc cga gat cct gtt aaa ctt cct aca aca gca   1104
Thr Gln Glu Pro Leu Gly Arg Asp Pro Val Lys Leu Pro Thr Thr Ala
        355                 360                 365 gcc agt acc cct gat gcc gtt gac aag tat ctc gag aca cct ggg gat   1152
Ala Ser Thr Pro Asp Ala Val Asp Lys Tyr Leu Glu Thr Pro Gly Asp
    370                 375                 380 gag aat gaa cat gcc cat ttc cag aaa gcc aaa gag agg ctt gag gcc   1200
Glu Asn Glu His Ala His Phe Gln Lys Ala Lys Glu Arg Leu Glu Ala
385                 390                 395                 400 aag cac cga gag aga atg tcc cag gtc atg aga gaa tgg gaa gag gca   1248
Lys His Arg Glu Arg Met Ser Gln Val Met Arg Glu Trp Glu Glu Ala
                405                 410                 415 gaa cgt caa gca aag aac ttg cct aaa gct gat aag aag gca gtt atc   1296
Glu Arg Gln Ala Lys Asn Leu Pro Lys Ala Asp Lys Lys Ala Val Ile
            420                 425                 430 cag cat ttc cag gag aaa gtg gaa tct ttg gaa cag gaa gca gcc aac   1344
Gln His Phe Gln Glu Lys Val Glu Ser Leu Glu Gln Glu Ala Ala Asn
        435                 440                 445 gag aga cag cag ctg gtg gag aca cac atg gcc aga gtg gaa gcc atg   1392
Glu Arg Gln Gln Leu Val Glu Thr His Met Ala Arg Val Glu Ala Met
    450                 455                 460 ctc aat gac cgc cgc cgc ctg gcc ctg gag aac tac atc acc gct ctg   1440
Leu Asn Asp Arg Arg Arg Leu Ala Leu Glu Asn Tyr Ile Thr Ala Leu
465                 470                 475                 480 cag gct gtt cct cct cgg cct cgt cac gtg ttc aat atg cta aag aag   1488
Gln Ala Val Pro Pro Arg Pro Arg His Val Phe Asn Met Leu Lys Lys
                485                 490                 495 tat gtc cgc gca gaa cag aag gac aga cag cac acc cta aag cat ttc   1536
Tyr Val Arg Ala Glu Gln Lys Asp Arg Gln His Thr Leu Lys His Phe
            500                 505                 510 gag cat gtg cgc atg gtg gat ccc aag aaa gcc gct cag atc cgg tcc   1584
Glu His Val Arg Met Val Asp Pro Lys Lys Ala Ala Gln Ile Arg Ser
        515                 520                 525 cag gtt atg aca cac ctc cgt gtg att tat gag cgc atg aat cag tct   1632
Gln Val Met Thr His Leu Arg Val Ile Tyr Glu Arg Met Asn Gln Ser
    530                 535                 540 ctc tcc ctg ctc tac aac gtg cct gca gtg gcc gag gag att cag gat   1680
Leu Ser Leu Leu Tyr Asn Val Pro Ala Val Ala Glu Glu Ile Gln Asp
545                 550                 555                 560 gaa gtt gat gag ctg ctt cag aaa gag caa aac tat tca gat gac gtc   1728
Glu Val Asp Glu Leu Leu Gln Lys Glu Gln Asn Tyr Ser Asp Asp Val
                565                 570                 575 ttg gcc aac atg att agt gaa cca agg atc agt tac gga aac gat gct   1776
Leu Ala Asn Met Ile Ser Glu Pro Arg Ile Ser Tyr Gly Asn Asp Ala
            580                 585                 590 ctc atg cca tct ttg acc gaa acg aaa acc acc gtg gag ctc ctt ccc   1824
Leu Met Pro Ser Leu Thr Glu Thr Lys Thr Thr Val Glu Leu Leu Pro
        595                 600                 605
```

```
gtg aat gga gag ttc agc ctg gac gat ctc cag ccg tgg cat tct ttt      1872
Val Asn Gly Glu Phe Ser Leu Asp Asp Leu Gln Pro Trp His Ser Phe
    610                 615                 620 ggg gct gac tct gtg cca gcc aac aca gaa aac gaa gtt gag cct gtt      1920
Gly Ala Asp Ser Val Pro Ala Asn Thr Glu Asn Glu Val Glu Pro Val
625                 630                 635                 640 gat gcc cgc cct gct gcc gac cga gga ctg acc act cga cca ggt tct      1968
Asp Ala Arg Pro Ala Ala Asp Arg Gly Leu Thr Thr Arg Pro Gly Ser
                645                 650                 655 ggg ttg aca aat atc aag acg gag gag atc tct gaa gtg aag atg gat      2016
Gly Leu Thr Asn Ile Lys Thr Glu Glu Ile Ser Glu Val Lys Met Asp
            660                 665                 670 gca gaa ttc cga cat gac tca gga tat gaa gtt cat cat caa aaa ttg      2064
Ala Glu Phe Arg His Asp Ser Gly Tyr Glu Val His His Gln Lys Leu
        675                 680                 685 gtg ttc ttt gca gaa gat gtg ggt tca aac aaa ggt gca atc att gga      2112
Val Phe Phe Ala Glu Asp Val Gly Ser Asn Lys Gly Ala Ile Ile Gly
    690                 695                 700 ctc atg gtg ggc ggt gtt gtc ata gcg aca gtg atc gtc atc acc ttg      2160
Leu Met Val Gly Gly Val Val Ile Ala Thr Val Ile Val Ile Thr Leu
705                 710                 715                 720 gtg atg ctg aag aag aaa cag tac aca tcc att cat cat ggt gtg gtg      2208
Val Met Leu Lys Lys Lys Gln Tyr Thr Ser Ile His His Gly Val Val
                725                 730                 735 gag gtt gac gcc gct gtc acc cca gag gag cgc cac ctg tcc aag atg      2256
Glu Val Asp Ala Ala Val Thr Pro Glu Glu Arg His Leu Ser Lys Met
            740                 745                 750 cag cag aac ggc tac gaa aat cca acc tac aag ttc ttt gag cag atg      2304
Gln Gln Asn Gly Tyr Glu Asn Pro Thr Tyr Lys Phe Phe Glu Gln Met
        755                 760                 765 cag aac tag                                                          2313
Gln Asn
    770

<210> SEQ ID NO 9
<211> LENGTH: 770
<212> TYPE: PRT
<213> ORGANISM: Homo sapiens

<400> SEQUENCE: 9

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140
```

```
Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
            165                 170                 175

Asp Lys Phe Arg Gly Val Glu Phe Val Cys Cys Pro Leu Ala Glu Glu
        180                 185                 190

Ser Asp Asn Val Asp Ser Ala Asp Ala Glu Glu Asp Asp Ser Asp Val
    195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

Thr Gln Glu Pro Leu Gly Arg Asp Pro Val Lys Leu Pro Thr Thr Ala
        355                 360                 365

Ala Ser Thr Pro Asp Ala Val Asp Lys Tyr Leu Glu Thr Pro Gly Asp
370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
530                 535                 540

Leu Ser Leu Leu Tyr Asn Val Pro Ala Val Ala Glu Glu Ile Gln Asp
545                 550                 555                 560
```

-continued

```
Glu Val Asp Glu Leu Leu Gln Lys Glu Gln Asn Tyr Ser Asp Asp Val
            565                 570                 575

Leu Ala Asn Met Ile Ser Glu Pro Arg Ile Ser Tyr Gly Asn Asp Ala
        580                 585                 590

Leu Met Pro Ser Leu Thr Glu Thr Lys Thr Val Glu Leu Leu Pro
    595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
            645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
            675                 680                 685

Val Phe Phe Ala Glu Asp Val Gly Ser Asn Lys Gly Ala Ile Ile Gly
            690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
            725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
            755                 760                 765

Gln Asn
    770

<210> SEQ ID NO 10
<211> LENGTH: 10
<212> TYPE: PRT
<213> ORGANISM: Homo sapiens

<400> SEQUENCE: 10

Val Val Ile Ala Thr Val Ile Val Ile Thr
1               5                   10

<210> SEQ ID NO 11
<211> LENGTH: 11
<212> TYPE: PRT
<213> ORGANISM: Homo sapiens

<400> SEQUENCE: 11

Val Val Ile Ala Thr Val Ile Val Ile Thr Leu
1               5                   10

<210> SEQ ID NO 12
<211> LENGTH: 7
<212> TYPE: PRT
<213> ORGANISM: Homo sapiens

<400> SEQUENCE: 12

Leu Val Met Leu Lys Lys Lys
1               5

<210> SEQ ID NO 13
<211> LENGTH: 6
<212> TYPE: PRT
```

```
<213> ORGANISM: Homo sapiens

<400> SEQUENCE: 13

Val Met Leu Lys Lys Lys
1               5
```

GAMMA-SECRETASE INHIBITORS

TECHNICAL FIELD

The present invention relates to compounds that inhibit gamma-secretease, a splitting enzyme that produces amyloid protein from the amyloid-precursor protein. More specifically, the present invention relates to those compounds or their pharmaceutically acceptable salts, gamma-secretase inhibitors comprising them, use of the compounds in the screening of anti-aging drugs or antidementia drugs, as well as antibodies to the compounds.

BACKGROUND ART

Amyloid protein accumulation is a histopathological change occurring in cerebral tissues of not only those with Alzheimer's disease or Down's syndrome but also those who went through a process of normally aging. The amyloid protein, which consists of from 40 to 42/43 amino acids rich in hydrophobic ones, is produced from its precursor, the amyloid-precursor protein (hereinafter referred to as APP), by a hydrolytic cleavage. APP, which consists of 695, 751 or 770 amino acids, is a type 1 membrane protein that spans the membrane once, with its amino terminal portion exposed outside the cell. The difference in the number of its amino acids corresponds to the presence or absence of a so-called Kunitz-type protease inhibitor-active site, which is located in the region outside the cell. In neurocytes, a form of APP consisting of 695 amino acids (hereinafter referred to as "APP695", whose amino acid sequence is set forth as SEQ ID NO:7), is a dominant one. The APP695, consisting of 695 amino acids starting with the methionine at position 1 and extending up to the asparagine at position 695, is an isoform occurring mainly in neurocytes, and is a type 1 membrane protein having a transmembrane domain (consisting of 24 amino acid extending from the glycine at position 625 to the leucine at position 648) which spans the cell membrane once. The amyloid protein comprises a shorter form protein molecule consisting of 40 amino acids extending from the aspartic acid at position 597 in the APP695's portion exposed outside the cell to the valine at position 636, which is within the cell membrane, and a longer protein molecule consisting of 42 or 43 amino acids extending up to the alanine at position 638 or the threonine at position 639.

On the other hand, a form of APP consisting of 770 amino acids (hereinafter referred to as "APP770", whose nucleotide sequence in the coding region is set forth as SEQ ID NO:8 and whose amino acid sequence as SEQ ID NO:9) is an APP gene product consisting of 770 amino acids extending from the methionine at position 1 to the asparagine at position 770 and includes in it an amino acid sequence portion that the APP695 does not possess (75 amino acids extending from the glutamic acid at position 289 to the lysine at position 363). Apart from this inserted amino acid sequence, it is the molecule having exactly the same amino acid sequence as those of APP695. Besides the APP695 and the APP770, there is an isoform called APP751, which consists in total of 751 amino acids, with 19 amino acids lost that extends from the methionine at position 345 to the lysine at position 363 of the APP770. An amino acid sequence that is commonly inserted into APP751 and APP770 (56 amino acids extending from the glutamic acid at position 289 to the alanine at position 344 in the APP770 amino acid sequence) possesses an activity of the Kunitz-type protease inhibitor and is thought to be expressed in cells other than neurocytes.

Since a hypothesis was experimentally proven that toxicity on neurocytes is one of the physiological activities of the amyloid protein [Yankner,-B-A; Dawes,-L-R; Fisher,-S; Villa-Komaroff,-L; Oster-Granite,-M-L; Neve,-R-L. Neurotoxicity of a fragment of the amyloid precursor associated with Alzheimer's disease. (1989) Science. 245(4916): 417-20, and Yankner,-B-A; Duffy,-L-K; Kirschner,-D-A. Neurotrophic and neurotoxic effects of amyloid beta protein: reversal by tachykinin neuropeptides. (1990) Science. 1990 250(4978): 279-82], it has been assumed as a key molecule of the onset of Alzheimer's disease. Two important steps of reactions must take place for the amyloid protein to be produced from the amyloid-precursor protein. The first step is the cutting off, by β-secretase, of the portion extending from the amino terminus of the amyloid protein portion. At the second step, cleavage takes place at the carboxyl terminus of the amyloid protein by the action of γ-secretase, resulting in the release of the amyloid protein, with dissociated APP intracellular fragment left behind. According to conventional findings, the cleavage in the second step has been assumed to occur at the gamma (γ) site, which is at the carboxyl terminus of the amyloid protein (between the valine at position 711 and the isoleucine at position 712, between alanine at position 713 and the threonine at position 714, or between the threonine at position 714 and the valine at position 715, according to the manner of numbering of amino acid residues in the APP770). In recent findings, however, it is reported that the cleavage occurs at the upsilon (ε) site, downstream by further 5-10 amino acid residues (in the direction of the carboxyl terminus), and thus more close to the cytoplasm (between the threonine at position 719 and the leucine at position 720, or between the leucine at position 720 and the valine at position 721, according to the manner of numbering of amino acid residues in the APP770).

In Alzheimer's disease, neuronal lesions in the brain occur before its abnormal clinical symptoms will appear, such as disorientation, debilitating memory loss, amnesia, deteriorating judgment, and behavioral aberration. The neuronal lesions include deposition of the amyloid protein, neurofibrillary tangle, and degenerative cellular loss, among which deposition of the amyloid protein is the earliest pathological event.

The amyloid hypothesis, according to which the production and deposition of amyloid protein does cause the disease, is deemed important with respect to the progress of Alzheimer's disease. The basis for it has been provided by studies of familial Alzheimer's disease.

There is a speculation yet to be confirmed that γ-secretase is the gene product of presenilin-1 [Sherrington,-R; Rogaev,-E-I; Liang,-Y; Rogaeva,-E-A; Levesque,-G; Ikeda,-M; Chi,-H; Lin,-C; Li,-G; Holman,-K; et-al. Cloning of a gene bearing missense mutations in early-onset familial Alzheimer's disease. (1995) Nature, 375(6534), 754-760] and presenilin-2 [Levy-Lahad,-E; Wasco,-W; Poorkaj,-P; Romano,-D-M; Oshima,-J; Pettingell,-W-H; Yu,-C-E; Jondro,-P-D; Schmidt,-S-D; Wang,-K; et-al. Candidate gene for the chromosome 1 familial Alzheimer's disease locus. (1995) Science, 269(5226), 973-977, and Rogaev,-E-I; Sherrington,-R; Rogaeva,-E-A; Levesque,-G; Ikeda,-M; Liang,-Y; Chi,-H; Lin,-C; Holman,-K; Tsuda,-T; et-al. Familial Alzheimer's disease in kindreds with missense mutations in a gene on chromosome 1 related to the Alzheimer's disease type 3 gene, (1995) Nature 376(6543), 775-778], which were found on the chromosome 14 as causative genes of early-onset familial Alzheimer's disease.

That the APP is also a causative gene of early-onset familial Alzheimer's disease (Goate, A. et al Nature 1991) indicates that a plurality of genes are involved as causative factors of the single class of dementia called Alzheimer's disease.

As mentioned hereinbefore, the amyloid protein comprises two components. One is a shorter amyloid protein component, which starts with aspartic acid and ends in the valine at position 40, and the other is a longer amyloid protein component consisting of 42 or 43 amino acids, which starts with the same aspartic acid as does the 40 amino-acids component but ends in the alanine at position 42 (thus longer by 2 amino acid residues) or the threonine at position 43 (thus longer by 3 amino acid residues). The latter longer component is more hydrophobic and therefore still less soluble. Through addition of the shorter components around the longer one serving as a core, amyloid fiber is formed, which is a fibriform structure having the diameter of about 5 to 6 nm.

It has been demonstrated that the production of the longer amyloid protein increases where a genetic mutation occurs in presenilin-1 or presenilin-2. It is thus thought that this effect of mutation causes elevated formation of the longer amyloid protein component, which assumedly determines the threshold level of polymerization of the amyloid protein, and thereby accelerates the pathogenic reaction.

A number of genetic mutations in the APP have been identified, typical ones of which are roughly divided into Sweden mutation (Met670Asn, Lys671Leu, according to the manner of numbering of amino acid residues in the AP770. The same applies also to mutations described below.), Dutch-type mutation (Glu693Gln), London mutation (Val717Ile), and Australia mutation (Leu723Pro), which are located just before the position corresponding to the amino terminus of amyloid protein. While production of both components of the amyloid protein are found to increase in Sweden mutation, only the production of the longer amyloid protein component increases in London mutation and Australia mutation. The effect of Dutch-type mutation is still under discussion and no conclusion has been reached.

There is an allele E4, a risk factor relating to apolipoprotein E. Statistical analyses demonstrated that the onset of Alzheimer's disease will accelerated by 8 to 10 yeas where only one allele on the pair of chromosomes is E4, and by 16 to 20 years where the alleles are E4/E4 on the both chromosomes [Corder,-E-H; Saunders,-A-M; Strittmatter,-W-J; Schmechel,-D-E; Gaskell,-P-C; Small,-G-W; Roses,-A-D; Haines,-J-L; Pericak-Vance,-M-A., Gene dose of apolipoprotein E type 4 allele and the risk of Alzheimer's disease in late onset families, (1993) Science. 261(5123): 921-3].

It is assumed that inhibition of the activity of β-secretase and γ-secretase would suppress the production of amyloid protein, leading to therapeutic drugs that could halt or slow the progress of Alzheimer's disease. While a reaction of a-secretase, in addition to β-secretase, is also involved in the first step of APP hydrolysis, inhibition of the reaction of γ-secretase in the second step is expected to have an effect with wider spectrum, because that reaction commonly follows either type of the first step reaction.

Though final identification of γ-secretase is yet to be reached, it is demonstrated that presenilin-1 is playing an important role. According to animal experiments or cell culture experiments, defunctionalization of presenilin-1 reportedly caused abnormalities in the development of cranial nerves or the formation of spinal column, or abnormalities in the development of lymphocytes. Thus, presenilin-1 is known to have a variety of functions in addition to the one relating the amyloid protein.

It must be taken account that nonspecific suppression of γ-secretase's activity could trigger some severe side effects such as induction of cancer [Hardy, J., Israel, A. Alzheimer's disease, In search of gamma-secretase, (1999) Nature. 398 (6727) 466-7].

Presently known γ-secretase inhibitors are: inhibitors which are peptidomimetic compounds based on reports about the γ-site of the substrate APP, located at the carboxyl terminus of amyloid protein portion, on which the enzyme acts [Mori H., Takio K., Ogawara M. & Selkoe D. J. j, Mass spectrometry of purified amyloid b protein in Alzheimer's disease. (1992) J. Biol. Chem. 267, 17082-17086; Roher A. E., Lowenson J. D., Clarke S., Wolkow C., Wang R., Cotter R. J., Reardon I. M., Zurcher-Neely H. A., Heinrikson R. L., Ball M. J., et al. Structural alterations in the peptide backbone of beta-amyloid core protein may account for its deposition and stability in Alzheimer's disease. (1993) J Biol Chem. 268(5), 3072-3083] and enzyme inhibitors based on reports pointing out the importance of aspartic acid active site [Wolfe M. S., Xia W., Ostaszewski B. L., Diehl T. S., Kimberly W. T., Selkoe D. J. Two transmembrane aspartates in presenilin-1 required for presenilin endoproteolysis and gamma-secretase activity. (1999) Nature 398 (6727), 513-517].

As for a peptidomimetic compound, DFK-167 is known [Wolfe M. S., Citron M., Diehl T. S., Xia W., Donkor I. C. and Selkoe D. J.: A substrate-based difluoro ketone selectively inhibits Alzheimer's g-secretase activity. (1998) J. Med. Chem., 41(1), 6-9].

As for enzyme inhibitors, compounds screened from known inhibitors are reported. They are, L-685,458, which was made in the process of development of drugs for AIDS [Shearman, M. S., Beher, D., Clarke, E. E., Lewis, H. D., Harrison, T., Hunt, P., Nadin, A., Smith, A. L., Stevenson, G., Castro, J. L. L-685,458, an aspartyl protease transition state mimic, is a potent inhibitor of amyloid beta-protein precursor gamma-secretase activity. (2000) Biochemistry 39 (30), 8698-8704] and JLK-6, which is a α-chymotrypsin inhibitor [Nakajima, K., Powers, J. C., Ashe, B. M., Zimmerman, M. Mapping the extended substrate binding site of cathepsin G and human leukocyte elastase. Studies with peptide substrates related to the alpha 1-protease inhibitor reactive site. (1979) J. Biol. Chem. 254 (10), 4027-32].

Although the peptidomimetic compound-type inhibitors developed based on the γ-site of the substrate APP and the inhibitors developed based on the active site of the enzyme are all potent inhibitors of amyloid protein production, each has significant troubles. First, DFK-167 is an inhibitor that was designed for the γ-site and is a compound totally independent from the recent findings on the ε-site, thus it has a different target with regard to inhibitor designing. Inhibitors L-685,458 and JLK-6 are not compounds originally developed as specific inhibitors of γ-secretase involved in the production of the amyloid protein from the APP. Apart from the specificity problem as γ-secretase inhibitors, there are other problems concerning efficacy at the target tissue.

DISCLOSURE OF THE INVENTION

An objective of the present invention is to provide novel compounds that inhibit γ-secretase.

Another objective of the present invention is to provide γ-secretase inhibitor compounds which is focused on the amino acid sequence of substrate APP, not on γ-secretase itself.

A further objective of the present invention is to provide γ-secretase inhibitor compounds based on the most recent findings about the ε-site.

A still further objective of the present invention is to provide a method for diagnosis, useful therapeutic drugs and method for treatment, and a method for screening for the development of useful therapeutic drugs, of Alzheimer's disease and other related diseases. The related diseases referred to herein includes diseases in which the amyloid protein is known or suspected to be directly or indirectly involved as the pathogen, like Down syndrome, as well as diseases in which amyloid protein is noted in the neuropathological lesions.

As a result of repeated exercise of ingenuity focused on the ε-site of APP (as opposed to the γ-site) in light of the findings of related studies, it was found that inhibition of γ-secretase and suppression of production of amyloid protein are brought about by a class of peptide-like compounds which have a similar chemical structure to a sequence made of several amino acid including the ε-site of the APP but in which a peptide bond is replaced with a bond stable to the enzyme between the Leu located at the ε-site (the site where enzymatic cleavage takes place) and an amino acid located immediately before or after it. The present invention was accomplished based on the finding.

Thus, the present invention provides:

(1) a compound consisting of an amino acid sequence which consists of at least three consecutive amino acids of the amino acid sequence Val-Val-Ile-Ala-Thr-Val-Ile-Ile-Thr-Leu-Val-Met-Leu-Lys-Lys-Lys (SEQ ID NO:1) including Leu at position 11, wherein, between the Leu and one or both amino acids located immediately before or after it, the peptide bond, —CO—NH—, is replaced with a hydroxyethylene group, —CHOH—CH$_2$—, while any other inter amino-acid bond is a peptide bond, wherein the N terminus has an alkyloxycarbonyl group based on C1-10 alkyl that may carry phenyl or naphthyl as a substituent group, wherein the C terminus is converted to an alkyl ester or alkyl amide based on C1-10 alkyl that may carry phenyl or naphthyl as a substituent group, and wherein the hydrogen atom of the hydroxyl group of the Thr at position 10 may be replaced with a C1-4 hydrophobic group or a Z group, or a pharmaceutically acceptable salt thereof, (2) the compound as described in (1) above, wherein the Leu at position 14 of the amino acid sequence is replaced with a hydrophobic amino acid that may be Ile or with Pro, the Leu at position 11 is replaced with a hydrophobic amino acid that may be Ile, or the Thr at position 10 is replaced with Ser, or the Ile at position 9 is replaced with a hydrophobic amino acid that may be Leu, or a pharmaceutically acceptable salt thereof, (3) a compound consisting of an amino acid sequence which consists of 3, 4, 5 or 6 consecutive amino acids of the amino acid sequence Ile-Thr-Leu-Val-Met-Leu (SEQ ID NO:2) including the Leu at position 3, wherein, between the Leu and one or both amino acids located immediately before or after it, the peptide bond, —CO—NH—, is replaced with a hydroxyethylene group, —CHOH—CH$_2$—, while any other inter amino-acid bond is a peptide bond, wherein the N terminus has an alkyloxycarbonyl group based on C1-10 alkyl that may carry phenyl or naphthyl as a substituent group, wherein the C terminus is converted to an alkyl ester or alkyl amide based on C1-10 alkyl that may carry phenyl or naphthyl as a substituent group, and wherein the hydrogen atom of the hydroxyl group of the Thr may be replaced with a C1-4 hydrophobic group or a Z group, or a pharmaceutically acceptable salt thereof, (4) a compound consisting of the amino acid sequence Leu-Val-Met-Leu (SEQ ID NO:3), wherein, between the Leu at position 1 and the Val at position 2, the peptide bond, —CO—NH—, is replaced with a hydroxyethylene group, —CHOH—CH$_2$—, while any other inter amino-acid bond is a peptide bond, wherein the N terminus has an alkyloxycarbonyl group based on C1-10 alkyl that may carry phenyl or naphthyl as a substituent group, wherein the C terminus is converted to an alkyl ester or alkyl amide based on C1-10 alkyl that may carry phenyl or naphthyl as a substituent group, or a pharmaceutically acceptable salt thereof, (5) a compound consisting of the amino acid sequence Thr-Leu-Val-Met (SEQ ID NO:4), wherein, between the Thr at position 1 and Leu at position 2, the peptide bond, —CO—NH—, is replaced with a hydroxyethylene group, —CHOH—CH$_2$—, while any other inter amino-acid bond is a peptide bond, wherein the N terminus has an alkyloxycarbonyl group based on C1-10 alkyl that may carry phenyl or naphthyl as a substituent group, wherein the C terminus is converted to an alkyl ester or alkyl amide based on C1-10 alkyl that may carry phenyl or naphthyl as a substituent group, and wherein the hydrogen atom of the hydroxyl group of the Thr may be replaced with a C1-4 hydrophobic group or a Z group, or a pharmaceutically acceptable salt thereof, (6) the compound described in (3) above, wherein the Leu located immediately before the Val is replaced with a hydrophobic amino acid that may be Ile, or the Leu at the N terminus is replaced with a hydrophobic amino acid that may be Ile or with Pro, or a pharmaceutically acceptable salt thereof, (7) the compound described in (4) above, wherein the Leu located immediately before the Val is replaced with a hydrophobic amino acid that may be Ile, or the Leu at the N terminus is replaced with a hydrophobic amino acid that may be Ile or with Pro, or a pharmaceutically acceptable salt thereof, (8) the compound described in (5) above, wherein the Leu located immediately before the Val is replaced with a hydrophobic amino acid that may be Ile, or a pharmaceutically acceptable salt thereof, (9) the compound described in (3) above, wherein the Thr is replaced with Ser, or a pharmaceutically acceptable salt thereof,

(10) the compound described in (3) above, wherein the Ile is replaced with a hydrophobic amino acid that may be Leu, or a pharmaceutically acceptable salt thereof,

(11) the compound described in (5) above, wherein the Thr is replaced with Ser, or a pharmaceutically acceptable salt thereof,

(12) the compound of one of (1) to (11) above, wherein the alkyloxycarbonyl group is a Boc group, or a pharmaceutically acceptable salt thereof,

(13) the compound described in one of (1) to (12) above, wherein a polypeptide consisting of Tyr-Gly-Arg-Lys-Lys-Arg-Arg-Gln-Arg-Arg-Arg (SEQ ID NO:5) is fused instead of the alkyloxycarbonyl group, or a pharmaceutically acceptable salt thereof,

(14) a gamma-secretase inhibitor comprising the compound described in one of (1) to (13) above,

(15) an antibody to the compound described in one of (1) to (13) above, (16) use of the compound described in one of (1) to (13) above as a gamma-secretase inhibitor in the screening of an inhibitor of amyloid protein production.

The compounds of the present invention and acceptable salts thereof may be used for the treatment of, and for the screening of therapeutic drugs of, Alzheimer's disease and related diseases thereto, such as those in which amyloid protein is known or suspected to be directly or indirectly involved as a causative factor of the disease, e.g., Down syndrome, and diseases in which amyloid protein is observed at a site of a neuropathological lesion. In addition, the antibody of the present invention may be used, e.g., for determining the blood levels of the compound of the present invention administered to a human for treatment.

BEST MODE FOR CARRYING OUT THE INVENTION

Figure 1:
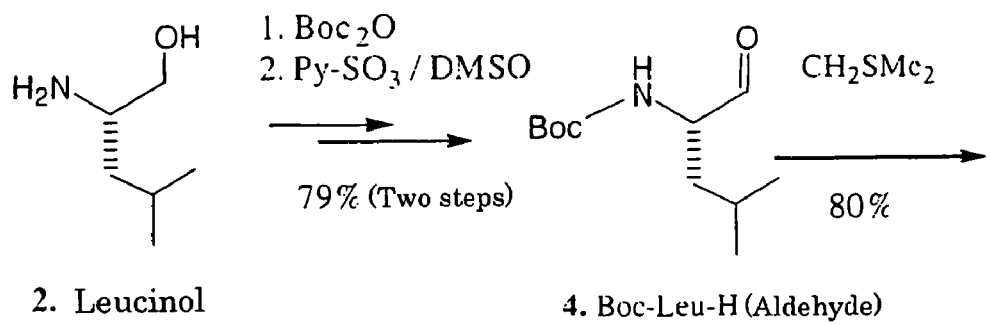
FIG. 1 shows the first part of a flowchart illustrating the process of synthesis.

In the present invention, the "allyl" referred to in connection with the alkyloxycarbonyl group is a C1-10, preferably C1-7, and more preferably C1-5 alkyl. Such an alkyl may be linear or branched and, may be, e.g., methyl, ethyl, propyl, isopropyl, n-butyl, sec-butyl, t-butyl, n-pentyl, isopentyl, 2-methylbutyl, 2,2-dimethylpropyl, t-pentyl, hexyl, heptyl, octyl, nonyl, decyl, etc. One of the particularly preferred examples is t-butyl. They may have one or more of their hydrogen atoms replaced with a phenyl group or a naphthyl group. A particularly preferred example of such substituent groups is a benzyloxycarbonyl group.

In the present invention, the "alkyl" referred to in connection with the "conversion to an alkyl ester or alkyl amide" is a C1-10, preferably C1-7, and more preferably C1-5 alkyl. Such an alkyl may be linear or branched and, may be, e.g., methyl, ethyl, propyl, isopropyl, n-butyl, sec-butyl, t-butyl, n-pentyl, isopentyl, 2-methylbutyl, 2,2-dimethylpropyl, t-pentyl, hexyl, heptyl, octyl, nonyl, decyl, etc. Methyl and t-butyl are particularly preferred examples. They may have one or more of their hydrogen atoms replaced with a phenyl group or a naphthyl group. One of particularly preferred examples is a benzyloxycarbonyl group.

In the present invention, when the hydrogen atoms of the hydroxyl group of Thr are replaced with a C1-4 hydrophobic group or with a Z group (i.e., a carbobenzoxy group), examples of the C1-4 hydrophobic group includes hydrophobic protective groups such as methyl, ethyl, propyl, n-butyl, sec-butyl, t-butyl, etc.

In the present invention, an "amino acid" means an L-amino acid.

Based on a hypothesis set up in light of the findings from in-depth studies of APP degradation products, that a stabilized ε-site could inhibit γ-secretase, the peptidomimetic compounds of the present invention was obtained through an attempt of preparing a compound which has a structure similar to the ε-site but stabilized to the enzyme, and their suppressive effect was confirmed not only on sporadic Alzheimer's disease's amyloid production but also on amyloid production involving a gene mutation of early-onset familial Alzheimer's disease.

A variety of peptide-like compounds which have an amino acid sequence similar to that located around the ε-site of the APP cleaved by γ-secretase but are modified to stabilize the site and have a γ-secretase inhibiting activity, may be used for the purpose of the present invention. An example of such a compound is one in which an amino acid residue, —NH—CHR—CO—, in the vicinity of the ε-site is replaced with a different amino acid residue having a similar property regarding to the R (hydrophobicity/hydrophilicity, acidity/basicity, absence ore presence of sulfur atom, presence or absence of a hydroxy group, etc.), and which has a γ-secretase inhibiting activity. For example; Ile, Val, Ala and Gly are amino acids that may be substituted for Leu; Leu, Val, Ala and Gly for Ile; Ser for Thr; Ala for Met; Gly, Val, Ile and Leu for Ala; Arg and His for Lys, respectively. Furthermore, the Leu at position 14 of SEQ ID NO:1 (identical to the Leu at position 6 of SEQ ID NO:2 and the Leu at position 4 of SEQ ID NO:3) may be replaced with Pro, for it has been reported that the Aβ42 amyloid protein component increases in a variant in which the amino acid at that site is replaced with Pro (this suggests that such a variant protein has higher affinity to γ-secretase) [Kwok,-J-B; Li,-Q-X; Hallupp,-M; Whyte,-S; Ames,-D; Beyreuther,-K; Masters,-C-L; Schofield,-P-R, Novel Leu723Pro amyloid precursor protein mutation increases amyloid beta42(43) peptide levels and induces apoptosis. Ann-Neurol. 2000 February; 47(2): 249-53].

As raw materials for synthesizing the compound of the present invention and methods employed in each step of the synthesis are well known, one of ordinary skill in the art can prepare an aimed compound by carrying out synthesis, isolation, purification, etc. as desired. It is also possible to prepare a polypeptide part of the compound of the present invention by application of genetic recombination technology utilizing a host publicly known per se such as *E. coli*, yeast, *Bacillus subtilis*, insect cells, animal cells or plant cells. While chemical synthesis may be performed, for example, in accordance with the Examples that will be described hereinafter, any other method may be used insofar as it gives the aimed compound. For example, synthesis may be performed as desired by employing a combination of well-known methods such as Boc(t-butyloxycarbonyl)-carbonylation reaction, DMSO oxidation, alkaline reaction, acidic reaction, epoxidation, silica gel column chromatography, alkylation, saponification, reaction by heating, decarboxylation, condensation reaction, reverse-phase column chromatography, etc. Preferably, a method is employed in which each of the structural components of the compound of the present invention is sequentially reacted and the yield and the purity of the reactant is assayed at desired steps.

The compounds of the present invention may include such modifications as those for facilitating synthesis or purification, those for promoting physical/chemical stability, those for activation in the body relating to stability and instability or to conditioning to metabolism, and a modification for regulation which causes increase or decrease in the efficiency of transportation to organs including transportation across the blood-brain barrier. The "modification for regulation" referred to herein means a modification with a sequence consisting of the 11 amino acids, Tyr-Gly-Arg-Lys-Lys-Arg-Arg-Gln-Arg-Arg-Arg (SEQ ID NO:3) [Schwarze, S. R., Ho, A., Vocero-Akbani, A. & Dowdy, S. F. In vivo protein transduction: Delivery of a biologically active protein into the mouse Science 285: 1569-1572]. By having the regulating sequence linked via a peptide bond on its N terminus, the compound, thereby facilitated regarding its transport through the blood brain barrier, becomes capable of reaching more efficiently to a target site in the brain.

Other modifications of the compound of the present invention include, acetylation, acylation, ADP-ribosylation, amidation, attachment of a flavin compound via a covalent bond, attachment of a heme moiety via a covalent bond, attachment of a nucleotide or a nucleotide derivative via a covalent bond, attachment of a lipid or a lipid derivative via a covalent bond, attachment of phosphatidylinositol via a covalent bond, cross-linking, cyclization, disulfide bond formation, demethylation, formation of a cross-linking covalent bond, cystine formation, pyroglutamate formation, formylation, γ-carboxylation, glycosylation, GPI-anchor formation, hydroxylation, iodization, methylation, myristoylation, oxidation, protein hydrolysis processing, phosphorylation, prenylation, racemization, attachment of a lipid, sulfation, selenoylation, transfer RNA-mediated addition of an amino acid to the protein such as arginylation, and ubiquitination.

Furthermore, as it will be technically easy to perform structural addition, alteration or substitution in order to facilitate detection or purification of the compound of the present invention or its antibody, as well as to add any other function, any product obtained through such processing will fall within the scope of the present invention. Within the scope of the present invention will also fall genetically engineered products modified by addition of, e.g., FLAG-tag, β-galactosidase, alkaline phosphatase, an Fc fragment of immunoglobulins like IgG, and GFP.

[Antibody]

An antibody may be purified using, as an antigen, any compound chosen from the compound of the present invention, its derivatives and or decomposition products. An antigen may be the compound or its derivative, and consists of, e.g., 20 or less amino acid residues, preferably 5 or less amino acid residues, more preferably 3 and most preferably 2 amino acid residues. Purification may also be carried out using a combination of such antigens. An antigen need not to be the compound of the present invention itself or its derivative or decomposition product, but may be one of a structure having, outwardly exposed, a primary sequence in the vicinity of the APP's ε-site. The term "vicinity" referred to herein means a region extending by up to 4 amino acids from the ε-site, (which is at either of the 2 positions) in the direction of the carboxyl terminus.

For preparing an immunospecific antibody to the compound of the present invention or its derivative or decomposition compound, a compound containing the aforementioned amino acid sequence in the vicinity of the ε-site is preferably used as an antigen. Examples of preferable antibodies include:

(1) an antibody that recognizes the threonine at the carboxyl terminus of Val-Val-Ile-Ala-Thr-Val-Ile-Val-Ile-Thr (SEQ ID NO:10), (2) an antibody that recognizes the leucine located at the carboxyl terminus of Val-Val-Ile-Ala-Thr-Val-Ile-Val-Ile-Thr-Leu (SEQ ID NO:11), (3) an antibody that recognizes the leucine at the amino terminus of Leu-Val-Met-Leu-Lys-Lys-Lys (SEQ ID NO:12), (4) an antibody that recognizes the valine at the amino terminus of Val-Met-Leu-Lys-Lys-Lys (SEQ ID NO:13), (5) an antibody prepared by using an antigen comprising at least two series of amino acids including those amino acids recognized in the sequences described in (1) to (4) above.

These antibodies are not limited to a specific class or amount insofar as they immunologically bind to or recognize the site of interest. Binding or recognition of an antibody is determined through publicly known antigen-antibody reactions. The term "immunospecific" means possessing substantially greater affinity to a compound of interest than to other relating proteins or compounds known in the prior art.

Using, as an antigen, the compound of the present invention or its derivative or decomposition product, alone or with a carrier to which it is bound or with which it is mixed, and in the presence or absence of an adjuvant, an antibody is prepared by induction of humoral and/or cellular immune response to the antigen. Otherwise, immuno response may be induced by immunologically stimulating lymphocytes, or their progenitor cells, in culture. Examples of a carrier, on the scope of which no particular limitation is imposed insofar as it has by itself no adverse effect on the host, include, but are not limited to, cellulose, physiological saline, buffered physiological saline, dextrose, water, glycerol, ethanol, polymerized amino acid, albumin and a mixture thereof. Suitable animals used for immunization are mice, rats, rabbits, goats, horses, bovines, etc. A polyclonal antibody may be obtained in the form of a serum by a publicly known method, or by a method for antibody recovery from a serum. Examples of preferably means include immunoaffinity chromatography.

Production of a monoclonal antibody are carried out either by first harvesting tissues (e.g., the spleen or lymph nodes) containing the antibody activity from animals or harvesting cultured cells immunized as above, and then introducing transformation into publicly known perpetually growing cells (e.g., a myeloma line such as P3X63Ag8). For example, hybridoma cells prepared from the above antibody producing cell and a perpetually growing cells are cloned, and a specific hybridoma cell is selected that is producing an antibody that specifically recognize the novel compound of the present invention, and the antibody is collected from the culture medium of the hybridoma. A variety of techniques for performing this can be enumerated such as those described as hybridoma method [Kohler G. and Milstein C. (1975) Nature 256, 495-497], trioma method [Kozbor et al. Immunology Today (1983) 4: 72], and EBV method [Cole et al. Monoclonal antibodies and cancer therapy, Alan R. Liss, Inc., (1985): 77-96].

The antibody mentioned above may be used for identification, detection and quantitative determination of the compound of the present invention or its derivative or decomposition compound, or for preparation and purification of the compounds utilizing affinity chromatography. The antibody mentioned above may be converted to a human-type antibody using a publicly known technique.

Specifically, the compound of the present invention or its derivative or decomposition compound, and a specific antibody to them having an activity to enhance the effect of the compound of the present invention, its derivative or decomposition product, are useful as a standard compound for screening of compounds in search of amyloid protein-inhibitor drugs, and also as a means for such screening.

By administering its effective amount to a patient of Alzheimer's disease or a related disease thereto, in a pharmaceutically acceptable carrier or without use of a carrier, the compound of the present invention is used in order to control the amount of amyloid protein production, thereby preventing or treating those diseases or ameliorating their symptoms. The compound of the present invention may be provided in a suitable preparation form that enhances the efficiency in the transportation of the compound to the encephalic tissues.

While a species of the compound of the present invention may be used alone, a plurality of them also may be used in combination. Moreover, a concomitant use is allowed with other compounds which are beneficial for the treatment. A preferred form of a pharmaceutical composition for systemic administration containing the compound of the present invention is an injection, above all, an intravenous injection. Other routes for injection, such as subcutaneous, intramuscular and intraperitoneal routes, may also be employed. Another means for systemic administration is transmucosal or transdermal administration utilizing a penetration enhancer such as bile salt, fuchsine acid or other surfactants. Furthermore, oral administration is possible when enteric-coating preparations or capsules are properly formulated. Topical administration of such a pharmaceutical composition is also possible, which may be in the form of a plaster, a paste or a gel.

Examples of assay methods utilizing an antibody to the compound of the present invention, its derivatives or decomposition products include radioimmunoassay, competitive binding assay, high-performance liquid chromatography, Western blot analysis and ELISA, etc. and their combinations.

EXAMPLES

While the present invention will be described in further detail below with reference to examples, it should be noted, however, that the present invention is not limited to those examples.

Example 1

Synthesis of the Compound Boc-Leu*-Val-Met-Leu-OMe

Figure 2:
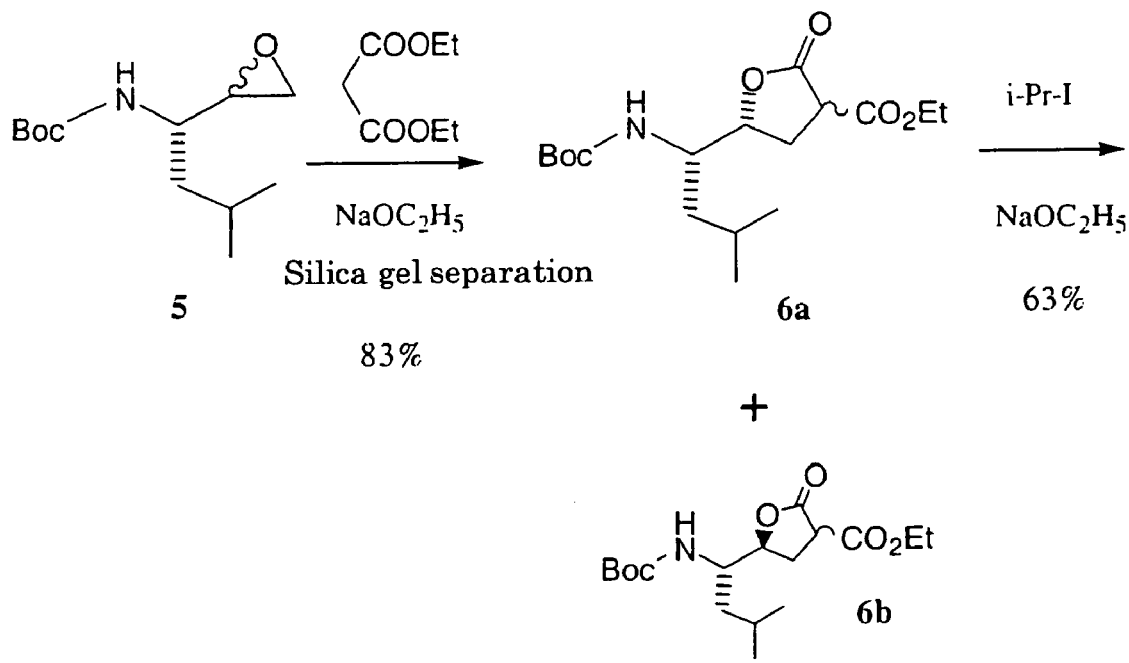
FIG. 2 shows a part of the flowchart that follows FIG. 1.
Figure 3:
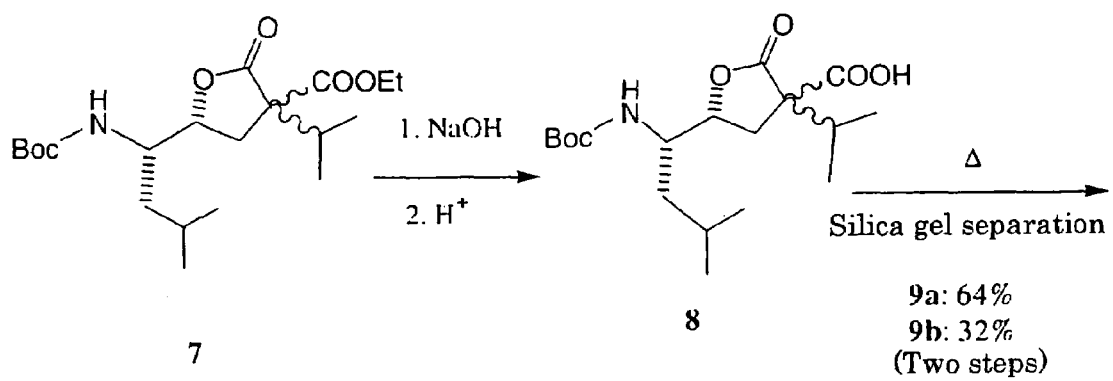
FIG. 3 shows a part of the flowchart that follows FIG. 2.
Figure 4:
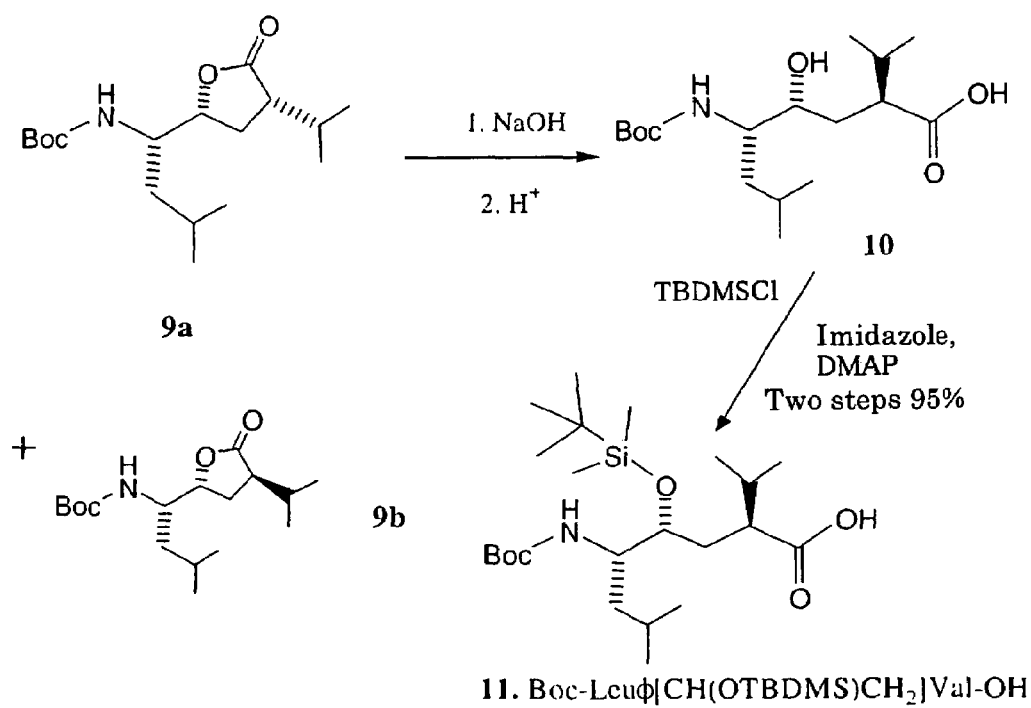
FIG. 4 shows a part of the flowchart that follows FIG. 3.
Figure 5:
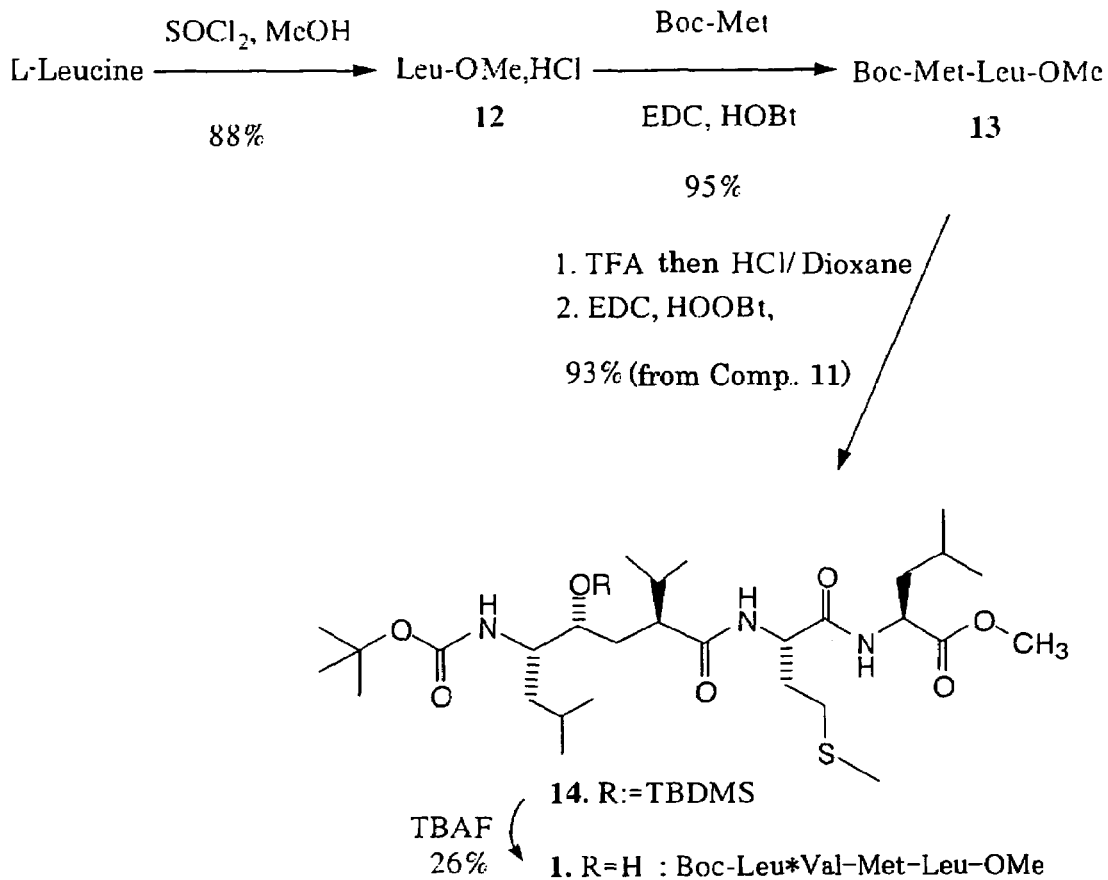
FIG. 5 shows the last part of the flowchart that follows FIG. 2.
Figure 6:
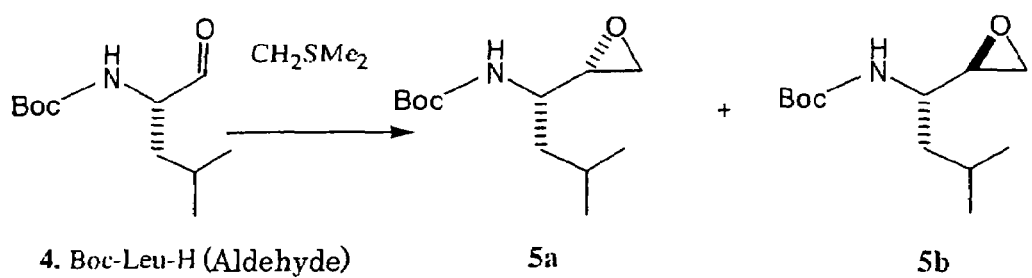
FIG. 6 illustrates the steps for the synthesis of Compound 5.

Boc-Leu*Val-Met-Leu-OMe (wherein, "*" indicates that the peptide bond "—CO—NH—" between the Leu and the Val is replaced with a hydroxyethylene group "—CHOH—CH$_2$—") was synthesized as follows according to the synthetic scheme shown in FIGS. 1-5. The compound was chosen in which the configuration around the α-carbon of the hydroxyethylene group represented the R-type. The structure of the compound is shown as the formula (1).

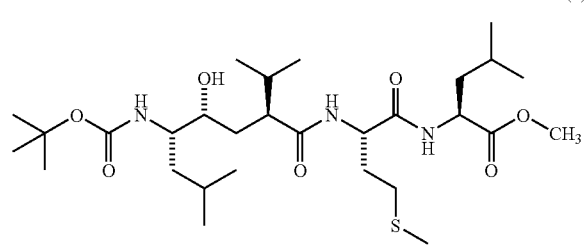

(1)

L-leucinol hydrochloric acid (2) (9.87 g, 64.2 mmol) was dissolved in 100 ml of acetone and 50 ml of water, and, after addition of triethylamine (21.5 ml, 128 mmol), refrigerated to −10° C. Boc$_2$O (20 g, 92 mmol) was added dropwise at −10° C. and then stirring was continued overnight without cooling. Acetone was evaporated and, following addition of about 500 ml of 0.1 M hydrochloric acid, extraction was carried out with 500 ml of ethyl acetate. The organic layer was washed with 0.1 M hydrochloric acid, water and then saturated saline solution in the order, and dried with anhydrous sodium sulfate. Following the removal of the drying agent, the organic layer was concentrated. Purification carried out using a silica gel open column (250 g, ethyl acetate/hexane=1/3) gave the aimed compound, Boc-leucinol (3). Yield: 12.88 g (92%).

Boc-leucinol (3) (12.88 g, 58.9 mmol) was flushed with toluene and then purged with argon gas. It was dissolved in dimethylsulfoxide (dehydrated, 200 ml) and, after addition of triethylamine (22 ml, 158 mmol), cooled in a 15° C. water bath. Meanwhile, in another flask, sulfur trioxide-pyridine complex (25.3 g, 159 mmol) was dissolved in dehydrated DMSO (100 ml) and stirred for 10 minutes under argon stream. Cooling at 15° C., the sulfur trioxide solution was added dropwise (4 minutes) to the solution of Boc-leucinol (3), and, after further stirring of 8 minutes, the reaction mixture was poured into 1500 ml of cold water to terminate the reaction. Following extraction with ethyl acetate, the organic layer was washed with 0.1 M hydrochloric acid, water and saturated saline solution in the order, dried with anhydrous sodium sulfate, and concentrated after removal of the drying agent. Purification using a silica gel open column (250 g, ethyl acetate/hexane=1/5) gave the aimed compound, Boc-Leu-H (aldehyde) (4). Yield: 10.9 g (85.8%).

Sodium hydride (62.6% in mineral oil), following removal of the 0.53 g mineral oil, was purged with argon gas. To this was added DMSO (dehydrated, 50 ml), and the mixture was then heated to 50° C., stirred for one hour, and, following addition of THF (dehydrated, 50 ml) to this, cooled on ice. A solution of (CH$_3$)SI (3.1 g, 15.2 mmol) in DMSO (15 ml) was added dropwise and, one minutes after the start of the addition, a solution of Boc-Leu-H (aldehyde) (4) (2.0 g, 9.3 mmol) in THF (10 ml) was added dropwise. After this dropwise addition was completed, the mixture was stirred for one hour without cooling. The reaction mixture was poured into 1000 ml of cold water to terminate the reaction, extracted with ethyl acetate, washed with water and saturated saline solution in the order and dried with anhydrous sodium sulfate. After removal of the drying agent by filtration, concentration performed gave 2.2 g of a crude product. Further, reaction of Boc-Leu-H (aldehyde) (4) (4.58 g, 21.3 mmol) under the same condition gave 4.81 g of a crude product (5a and 5b). The crude products from these duplicate reactions were combined and purified using a silica gel open column (ethyl acetate/hexane=1/2). Yield: 5.6 g (80%). This was separated using a silica gel open column (trichloromethane/acetone=100/1), the diastereomers s were purified, and fractions rich in 5a and 5b, respectively, were collected. Determination between the diastereomers 5a and 5b was performed by NMR. The 5a-rich fraction (5a/5b=5/1) was used in the following process.

Epoxy compound 5a (0.96 g, 4.2 mmol) and diethyl malonate (0.76 ml, 1.2 equivalents) were dissolved in 3 ml of ethanol (dehydrated), and, to the mixture was added dropwise 2 ml of 20% sodium ethoxide (3 equivalents) while cooling. Cooling then was terminated, and the mixture was stirred 20 hours at room temperature, and then poured into a cold aqueous solution of 10% citric acid to terminate the reaction. Extraction with ethyl acetate, washing with water and then saturated saline solution, drying with anhydrous sulfate, removal of the drying agent by filtration and purification on a silica gel column (ethyl acetate/hexane=1/5) gave compound 6a. Yield: 1.2 g (83%).

Under argon stream, compound 6a (1.13 g 3.29 mmol) was dissolved in 10 ml of dehydrated ethanol. To this were added, under cooling on ice, 20% sodium ethoxide (1.4 ml, 1.2 equivalents) and isopropyl iodide (1.8 ml, 3 equivalents).

After a five-hour stirring at 60° C., stirring was continued overnight at room temperature, and then 7 hours at 60° C. on the following day. The reaction was terminated by pouring the mixture into a 10% cold aqueous solution of citric acid. Extraction with ethyl acetate, washing of the organic layer, drying with sodium sulfate, removal of the drying agent by filtration and evaporation of the solvent gave a crude product. Purification using a silica gel column (20 g, ethyl acetate/hexane=1/3) gave the aimed compound 7. Yield: 0.8 g (63%).

Lactone-ester (7) (0.78 g, 2.0 mmol) was dissolved in about 10 ml of dioxane. Cooling on ice, 1 N sodium hydroxide (4 ml) was added dropwise and the mixture was stirred at room temperature. After a 1.5-hour stirring, dioxane was evaporated, and the residue was poured into a cold 0.2 N HCl aqueous solution, and extracted with ethyl acetate. The organic layer was washed with saturated saline solution, and dried over sodium sulfate. Filtered and concentrated, this gave a crude product of lactone-carboxylic acid (8). This was directly dissolved in toluene, and then heated on a 95° C. oil bath (3 hours), allowed to cool down overnight, and heated again 95° C. on the following day. One and a half hours later, toluene was evaporated and purification was performed using a silica gel column (ethyl acetate/hexane=1/5). Of two spatially approximate spots on the TLC of the products, 0.4 g of a compound (9a) corresponding to the lower spot and 0.2 g of a compound (9b) corresponding to the upper spot were obtained. Yield: 63% and 32%, respectively.

Compound 9a (0.37 g, 1.18 mmol) was dissolved in 2.5 ml of dioxane, and 1 N sodium hydroxide aqueous solution was added dropwise under ice-cooling, and stirred for 2 hours at room temperature. The reaction was then terminated by addition of a 20% aqueous solution of citric acid and extracted with ethyl acetate. The organic layer was washed with water and then with a saturated saline solution, dried with sodium sulfate, filtered and concentrated, thus giving hydroxycarboxylic acid (10). This was dissolved in anhydrous DMF, and after successive addition of imidazole (1.7 g, 25 mmol), t-butyldimethylsilyl chloride (1.8 g, 12 mmol) and DMAP (25 mg, 0.2 mmol), stirred overnight at room temperature. To this was added about 1 ml of methanol, and stirred for 30 minutes to kill the reagents. The mixture was poured into a 20% citric acid solution, and extracted with ethyl acetate. The organic layer was washed with water and then with saturated saline solution, dried with sodium sulfate, filtered and concentrated. This (disilyl compound) was dissolved in acetic acid and stirred for 4 hours at room temperature (cleavage of the silyl ester was confirmed by TLC and MS of the reaction mixture). After removal of acetic acid under reduced pressure, purification using a silica gel column (ethyl acetate/hexane=1/2) gave compound 11. Yield: 0.5 g (96%).

[Synthesis of an Isomer of Compound 11]

Starting with 9b, the same process as above gave an isomer of silyl compound 11. Yield: 0.2 g (88%).

[Synthesis of Hydrochloric Acid Salt of Leu-OMe]

Anhydrous methanol (150 ml) was placed in a flask and cooled down (−15° C.). To this was added $SOCl_2$ (40 ml) dropwise, and 10 minutes later L-leucine powder was directly added, and, with the cooling terminated, stirred at room temperature. About ten minutes later, further 100 ml of anhydrous methanol was added and stirring was continued overnight. Twenty hours later, the solvent was evaporated under reduced pressure, and, after flushing with methanol twice, diethyl ether was added to the crystalline residue. Precipitates were collected by filtration and dried over sodium hydroxide under reduced pressure. Yield: 24.23 g (87.8%).

[Synthesis of Boc-Met-Leu-OMe]

HCl, Leu-OMe (5.3 g, 29.2 mmol), Boc-Met (7.64 g, 30.6 mmol) and 1-hydroxy-1H-benzotriazole (HOBt) (4.34 g, 32 mmol) were weighed into a 500-ml flask, and dissolved in DMF. While cooling, WSCD (5.88 ml, 32 mmol) wad added dropwise. Two hours later, the mixture was poured into a cold 2% sodium bicarbonate aqueous solution, and precipitating crystals were collected by filtration and washed with water. They were dissolved in 300 ml of ethyl acetate and washed with 0.2 N hydrochloric acid, water and then saturated saline solution, and dried with sodium sulfate. After evaporation of the solvent, precipitated crystals were collected by filtration using hexane. Dried over phosphorus pentoxide, the aimed compound (13) was obtained. Yield: 10.4 g (94.6%).

[Process for Boc Removal]

While cooling, TFA was added to Boc-Met-Leu-OMe (1.09 g, 2.89 mmol), and 10 minutes later, the cooling was terminated and stirring was continued for 50 minutes at room temperature. TFA was evaporated and 4.9 N hydrochloric acid/dioxane (0.71 ml) was added. After several times decantation with hexane, concentration to dryness under reduced pressure gave a solid. Yield: 0.8 g (90% as hydrochloride).

[Condensation Reaction]

To the above hydrochloride (0.29 g, 0.93 mmol) were added compound 11 (0.34 g, 0.76 mmol) and HOOBt (150 mg, 0.92 mmol) and the mixture was dissolved in DMF (10 ml). While cooling, WSCD (170 µl, 0.93 mmol) was added dropwise, and, with the cooling terminated, stirred was continued at room temperature. Twenty hours later, the mixture was poured into a cold 2% aqueous solution of sodium bicarbonate to terminate the reaction. The mixture was extracted with ethyl acetate and washed with a 10% citric acid, water and saline solution. After drying with sodium sulfate, concentration and purification using a silica gel column (ethyl acetate/hexane=1/4) gave compound 14. Yield: 0.5 g (93%).

The protected compound 14 (0.5 g, 15-02011221) was dissolved anhydrous THF. This was desilylated by addition of TBAF-3$H_2$O (330 mg, 1.05 mmol), followed by a 24-hour stirring at room temperature. After evaporation of THF, purification using a silica gel column (ethyl acetate/hexane=1/1-1/2) gave 0.25 g of a crude product of aimed compound (1), with 0.14 g of the starting material recovered. Purification by reverse-phase HPLC (YMC—ODS, acetonitrile/water/0.1% TFA), and lyophilization gave the aimed compound. Yield: 106 mg (25%). ESI-MS: 590.3(M+H, Calculated value 590.38), 612.3 (M+Na).

[Synthesis of an Isomer of Compound 1]

Using the aforementioned isomer (0.18 g) of compound 11, condensation, removal of the protective group, and purification in the same manner gave 46 mg of an isomer of compound 1. ESI-MS: 590.3(M+H, Calculated value 590.38), 612.3(M+Na).

Example 2

Examination of Solubility

The compound synthesized in Example 1 was examined for its solubility, visually as well as by microscopy. The results are shown in the table below.

TABLE 1

Solubility of the Compound

| Solvent | Concentration (10 ng/ml) | Concentration (1 µg/ml) | Concentration (100 µg/ml) |
|---|---|---|---|
| Physiological saline | + | +/− | − |
| Phosphate buffer (pH 7.0) | + | +/− | − |
| DMEM medium containing 10% fetal bovine serum | + | +/− | − |
| DMSO | + | + | + |

+, dissolved; +/−, nearly dissolved, −, not dissolved

Example 3

Determination of Inhibitory Activity

The human APP695 gene used in this example (whose nucleotide sequence in its coding region is shown as SEQ ID NO:6) was what had been screened from a cDNA library prepared from the dead brain of a normal human by a conventional method, and its entire nucleotide sequence was confirmed by a conventional method. Briefly, about 1 g of frozen cerebral tissue was phenol-treated and the supernatant aqueous solution was collected. After repeating this process, mRNA was precipitated by addition of ethanol. After dissolving in 20 mM tris-HCl, pH 8., 0.1 mM EDTA, cDNA was synthesized with reverse transcriptase using oligo-dT primers and the mRNA as a template. After remaining RNA was digested with RNase, using thus obtained single-stranded cDNA as a template, double-stranded cDNA was synthesized with DNA polymerase. The double-stranded cDNA was then blunt-ended with T4 DNA polymerase. Following introduction of methylation into a EcoR1 restriction site using EcoR1 methylase, an EcoR1 linker adapter was ligated using ligase. After removal of unreacted free adapter by gel filtration, ligation to λgt11 vector was effected using DNA ligase, and thus ligated product was incorporated into λ-phage using a packaging kit. E. coli cells in agar plates were infected with the λ-phage thus obtained, and the solution containing thus proliferated phage was used as cDNA library. For APP cDNA cloning, oligonucleotides that were anticipated based on the amyloid protein were radio-labeled using $\gamma^{32}$P-ATP and DNA kinase to provide the labeled nucleotides as probes. $10^6$ pfu (plaque forming units) of phage were allowed to form plaques on agar plates, and brought into contact with a nylon membrane. The phage DNAs that stuck to the membrane were denatured to single-stranded DNAs by alkali treatment of the nylon membrane, and the membrane then was neutralized, to which, after incubation in a solution containing salmon sperm DNAs, the $^{32}$P radio-labeled nucleotide probes were added and allowed to hybridize for 12 hours. At this stage, where aimed APP gene incorporated to the phage and one of the oligonucleotides were mutually complementary in their sequences, they would form a double-stranded DNA. The nylon membrane was then exposed to X-ray film, and plaques on the agar plates corresponding to spots of exposure were identified with phages carrying APP gene (fragment). By repeating this process, a single phage was finally obtained. The nucleotide sequence of the APP gene incorporated into the phage was determined by publicly known Sanger method.

APP gene was efficiently introduced from outside into COS cells, which is a cultured cell line of simian kidney's origin, using Lipofectamine Plus reagent (Invitrogen K.K.) according to its protocol. Briefly, 1 µg of APP gene was dissolved in 100 µl of OPTI-MEM, mixed with 6 µl of Plus reagent and left to stand for 15 minutes at room temperature. In parallel, 4 µl of Lipofectamine dissolved in 100 µl of OPTI-MEM medium was prepared. This was then mixed with the APP gene solution, and left to stand for further 15 minutes. Six-well culture plates were provided in advance in each well of which was placed 800 µl of culture that had been prepared by culturing COS cells at 75% to 80% cell density in a DMEM medium supplemented with 10% fetal bovine serum, and then replacing the medium with OPTI-MEM medium. Two hundred pl of the reaction mixture containing the gene were added to each culture well. Twelve hours after introduction of the gene, the medium was changed from the OPTI-MEM medium containing the introduced gene to a 10% fetal bovine serum-supplemented DMEM medium free of the introduced gene. To this culture, the compound obtained in Example 1 was added. After 36 to 48 hours, culture supernatant was collected, transferred to centrifuging tubes, and centrifuged at 10,000 r.p.m. at room temperature for 5 minutes. The supernatant was used as a sample containing amyloid protein. The shorter and the longer amyloid protein components contained in each sample can be separately determined using a commercially available ELISA kit for amyloid protein determination (KHB3441: Signal Select™ Human ⊖ Amyloid1-42 ELISA Kit, or KHB3481: Signal Select™ Human β Amyloid1-40 ELISA Kit, BioSource International, Inc. CA, USA). Those ELISA kits for amyloid determination included 96-well ELISA plates coated with a primary antibody to these two types of amyloid proteins. Following eliminating non-specific antigen-antibody reactions by allowing a usual non-specific blocking reaction, a sample medium containing the amyloid protein to be measured was reacted. Then, after usual washing, one of secondary antibodies was added. The secondary antibodies consisted of two deferent antibodies that can distinguish between the two types of amyloid proteins, the one is the shorter amyloid protein and the other is the longer amyloid antibody, without no cross reactivity. The difference between the two amyloid proteins is the absence or presence of the two amino acid residues (isoleucine and alanine) at their carboxyl terminus. The antibody that detects the former is considered to recognize valine at the carboxyl terminus and the antibody that detects the latter is thought to recognize the alanine.

The results of the amyloid protein determination using the kit are shown in the following tables.

TABLE 2

Compound's Inhibitory Activity-1

| | | DMSO | | | Inhibitor (100 μM) | | |
|---|---|---|---|---|---|---|---|
| | | Aβ42(43) (pg/ml) | Aβ40 (pg/ml) | Ratio of Aβ42(43)/ Aβ40 | Aβ42(43) (pg/ml) | Aβ40 (pg/ml) | Ratio of Aβ42(43)/ Aβ40 |
| 1 | Mock treatment | 0 | 0 | — | 0 | 0 | — |
| 2 | Wild-type APP695 | 1415 | 9656 | 0.147 | 415 | 218 | 1.90 |
| 3 | London-type APP695 | 2845 | 6623 | 0.430 | 855 | 151 | 5.66 |
| 4 | Sweden-type APP695 | 2503 | 17002 | 0.147 | 1311 | 1726 | 0.76 |

TABLE 3

Compound's Inhibitory Activity-2

| | | Inhibition rate (%) | | |
|---|---|---|---|---|
| | | Aβ42(43) | Aβ42 | Total Aβ |
| 1 | Mock treatment | — | — | — |
| 2 | Wild-type APP695 | 71 | 98 | 98 |
| 3 | London-type APP695 | 70 | 98 | 89 |
| 4 | Sweden-type APP695 | 48 | 90 | 84 |

As evident from Tables 1 and 2, the inhibitor exhibited an inhibitory activities of about 71% for Aβ42(43) production and nearly 100%, i.e., about 98% for Aβ40 production. About 98% inhibition was achieved even on the total amyloid protein. Thus, it was revealed that the present inhibitor has an effective activity.

Although it is a rare class of disease comprising only several % of total Alzheimer's disease cases, inhibitory activity on amyloid protein production in familial early-onset Alzheimer's disease was also examined. According to the results, nearly the same level of inhibitory activity as that noted on the wild-type sequence was observed on Val717Ile mutation of amyloid protein, called London mutation. On the other hand, on a double mutation discovered in Sweden, Met670Arn and Lys671Leu, inhibitory activity was about 90% for Aβ40 and about 48% for Aβ42(43). On each mutation of the familial disease, more than about 80% inhibition was noted for total amyloid production.

Example 4

Determination of Inhibitory Activity

In Examination 3, a full sized human APP gene was employed. The amyloid protein is formed through proteolysis consisting of the first-step cleavage of the APP by α- or β-secretase and the second-step cleavage by γ-secretase. Besides γ-secretase inhibition, the inhibition in the first-step could lead to suppression of amyloid protein synthesis. In order to directly demonstrate that the inhibitory effect of the compound of the present invention is due to inhibition of γ-secretase (but not due to inhibition of β-secretase), an experiment was carried out in the same manner as in Example 4 except that an APP artificial fragment (referred to as C100), which lacked a polypeptide portion that is to be cut off in the first stage, was used instead of APP695, and amyloid protein thus produced was measured. The results are shown in the following table.

TABLE 4

Compound' Inhibitory Activity-3

| | | DMSO | | | Inhibitor (100 μM) | | | Inhibition rate (%) | | |
|---|---|---|---|---|---|---|---|---|---|---|
| | | Aβ42(43) (pg/ml) | Aβ40 (pg/ml) | Total Aβ (pg/ml) | Aβ42(43) (pg/ml) | Aβ40 (pg/ml) | Total Aβ | Aβ42 (43) | Aβ40 | Total Aβ |
| 1 | C100 | 127 | 944 | 1071 | 62 | 100 | 162 | 51 | 89 | 85 |

In the experiment using a C-100 APP (wild type), nearly the same inhibitory activity was observed as was in the Sweden-type mutation, i.e., about 90% inhibition for Aβ40 and about 50% inhibition for Aβ42(43). In each case where a familial disease-type mutation is present, more than about 80% of inhibition was observed on total production of amyloid protein.

Example 5

Synthesis of the Compound
t-But-OCO-Thr*-Leu-Val-Met-NH-Bzl

Figure 7:
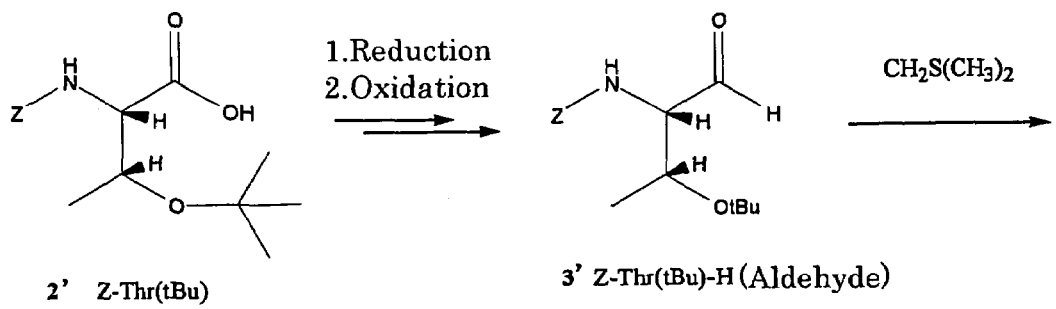
FIG. 7 shows the first part of a flowchart illustrating the process of synthesis of another compound.
Figure 8:
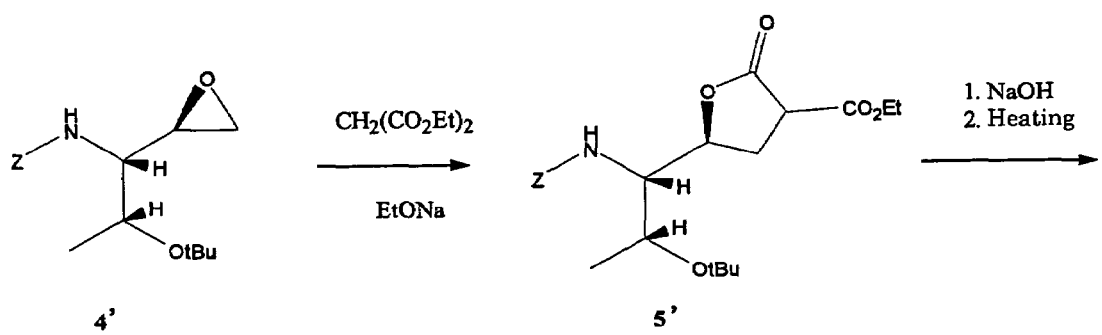
FIG. 8 shows a part of the flowchart that follows FIG. 7.
Figure 9:
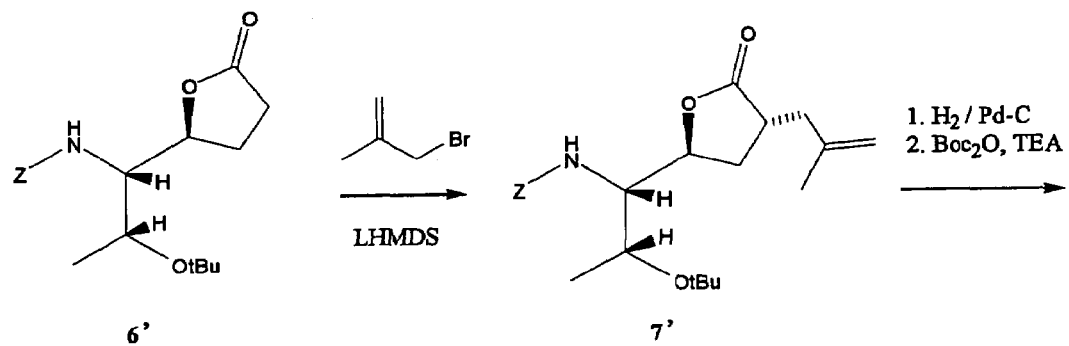
FIG. 9 shows a part of the flowchart that follows FIG. 8.
Figure 10:
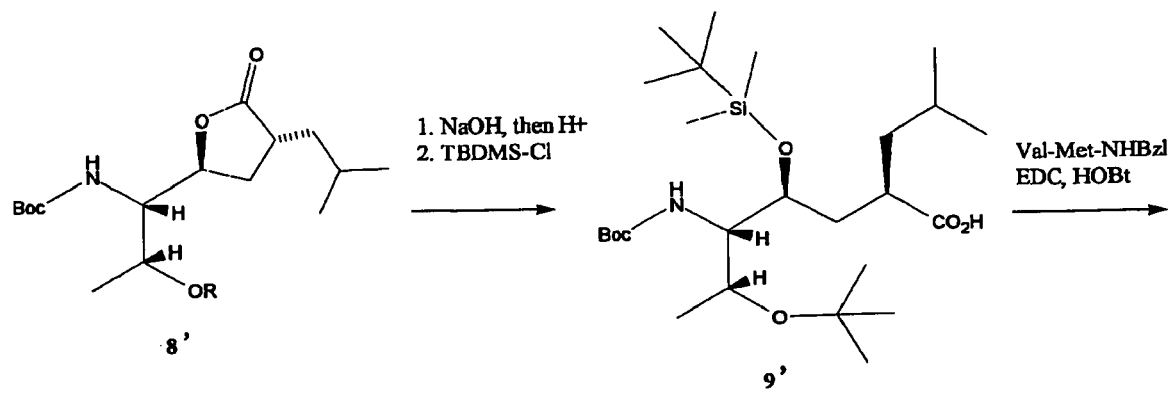
FIG. 10 shows a part of the flowchart that follows FIG. 9.
Figure 11:
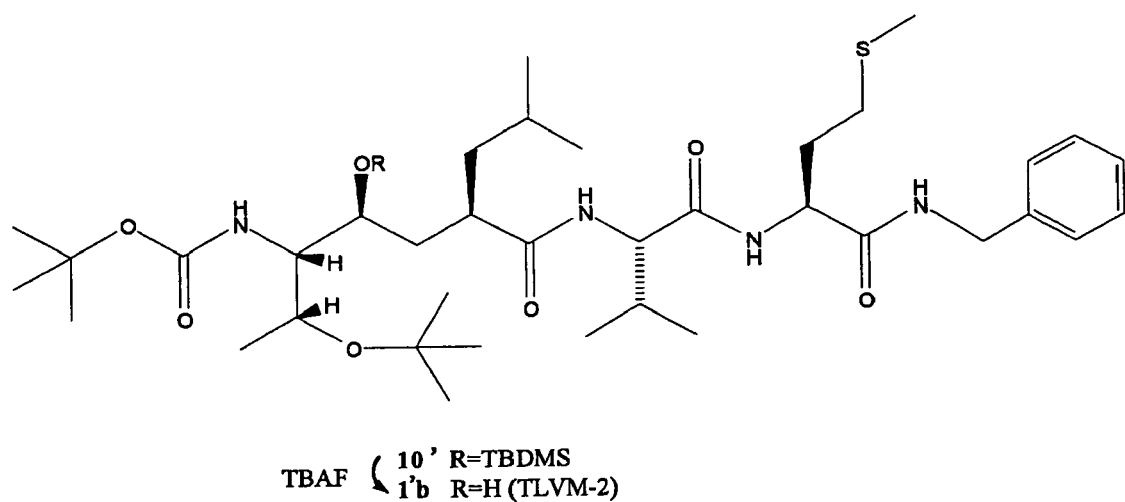
FIG. 11 shows a part of the flowchart that follows FIG. 10.
Figure 12:
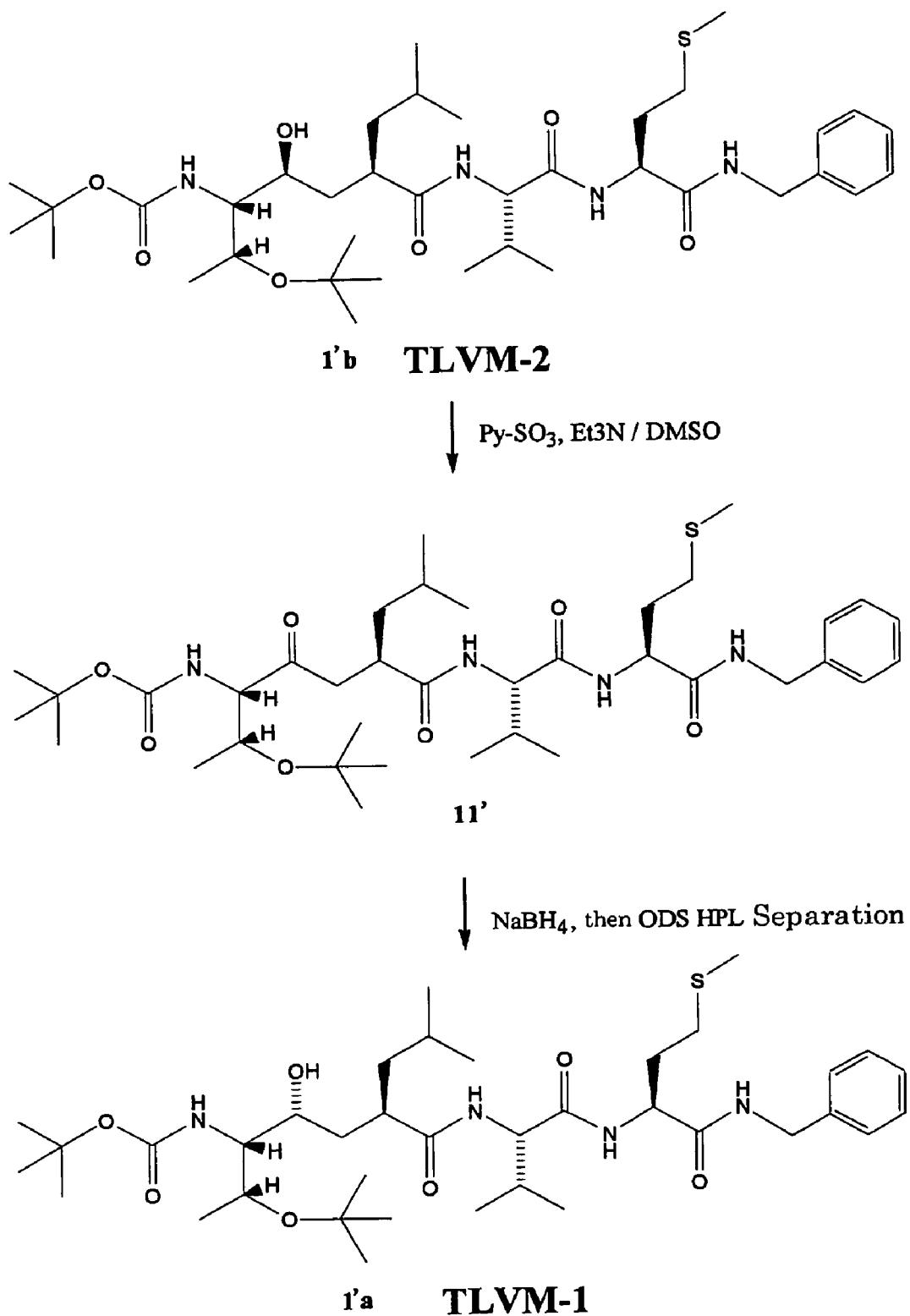
FIG. 12 shows the last part of the flowchart that follows FIG. 11.

T-But-OCO-Thr*-Leu-Val-Met-NH-Bzl (wherein, "*" indicates that the peptide bond "—CO—NH—" between the Thr and the Leu is replaced with a hydroxyethylene group "—CHOH—CH$_2$—" and that the hydroxyl group of the Thr is converted to t-butyl ether) was synthesized as follows according to the synthetic scheme shown in FIGS. 7-12. Both R- and S-type compounds were synthesized with regard to the configuration around α-carbon of the hydroxyethylene group of the compounds. Out of these, the R-type compound is shown in the formula (1a).

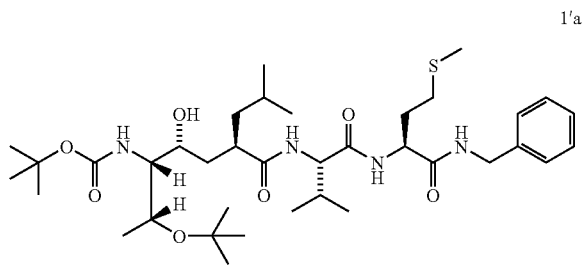

1'a

Synthesis of Aldehyde 3':

DCHA salt of 2' (49.5 g, 100.88 mmol) (Bachem 123400) was dissolved in ethyl acetate (500 ml), and demineralized with a 20% citric acid aqueous solution. The organic layer was washed with water (three times) and then saturated saline solution, dried with Na$_2$SO$_4$, and, after removal of the drying agent by filtration, concentrated to give a oily residue. The residue was then dissolved in anhydrous THF (500 ml), cooled to −15° C., and isobutyl chlorocarbonate (15.7 ml, 121 mmol) was added dropwise. After a 10-minute stirring at −15° C., NaBH$_4$ was added and, after stirring was continued for 10 minutes at −15° C., then cooled down to −50° C. and methanol (500 ml) was added dropwise. Following dropwise addition of 1 N hydrochloric acid (200 ml), the mixture was stirred for 30 minutes while letting it return to room temperature. After evaporation of the solvent, extraction with ethyl acetate, washing with 0.2 N hydrochloric acid, water (three times) and saturated purified water in the order, drying with Na$_2$SO$_4$ and evaporation of the solvent gave an alcohol (39 g). Thirty-nine g of this alcohol was divided into three portions and 13 g each were subjected to oxidizing reaction at a time. Briefly, Z-Thr(tBu)-ol (13 g, 33 mmol), after subjected twice to the process of dissolution in toluene and evaporation of the solvent, was dissolved in anhydrous DMSO (120 ml), and, after addition of triethylamine (13.9 ml, 100 mmol), cooled in a water bath at 15° C. Sulfur trioxide-pyridine complex (15.9 g, 100 mmol) was dissolved in DMSO (70 ml) in another flask, and the solution was added dropwise to the Z-Thr(tBu)-ol solution over 2 minutes. After 8 minutes of stirring in the 15° C. water bath, the reaction was terminated by pouring the mixture into ice-cold water. Extraction was carried out with ethyl acetate. The remaining portions of the alcohol were subjected to the reaction in the same manner. All the ethyl acetate extract was combined, washed with water and then saturated saline solution, dried with Na$_2$SO$_4$, concentrated, and purified using a silica gel column (AcOEt/Hex=1/4) to give the aimed aldehyde (3'). Yield: 24.1 g (81% from the carboxylic acid).

Synthesis of Epoxy Compound (4'):

The aldehyde (3'), divided into two halves, was subjected to reaction in twice. DMSO (anhydrous, 200 ml) was added to 1.9 g sodium hydride (62.6% in oil), and heated to 50° C. and stirred for one hour. To thus formed dimethylsulfinyl anion solution was added THF (anhydrous, 200 ml) and the mixture was cooed on ice. To this was added a DMSO solution (50 ml) of (CH$_3$)SI (10 g, 49 mmol) dropwise (over 20 seconds), and one minute after the start of the dropwise addition, a THF solution (510 ml) of Z-Thr(tBu)-H (12.0 g, 40.9 mmol) was added dropwise (over one minute). After the dropwise addition was finished, stirring was continued at room temperature (20° C.) for one hour and the reaction was terminated by pouring the mixture into 1500 ml of cold water. Extraction with ethyl acetate, washing with water and saturated saline solution in the order, drying with anhydrous sodium sulfate and concentration gave 10 g of crude product. A second series of reactions carried out in the same manner gave 10 g of crude product. The products of these two series of reactions were combined, purified using a silica gel column (AcOEt/Hex=1/2), and further purified using a silica gel column (AcOEt/Hex=1/4) to give the aimed epoxy compound (4'). 6.3 g (25%).

Synthesis of Compound (5):

The epoxy compound (4) (6.3 g, 20.5 mmol) was dissolved in anhydrous ethanol (10 ml) and, after addition of diethyl malonate (3.8 ml, 25 mmol), cooled on ice. While ice-cooling, 20% NaOEt (9.6 ml, 24.5 mmol) was added dropwise, and, after a 3-hour stirring, a 10% citric acid aqueous solution was added. Extraction was performed with ethyl acetate, and the ethyl acetate layer was washed with water and then with saturated saline solution, dried with Na$_2$SO$_4$, concentrated, and purified using a silica gel column (AcOEt/Hex=1/2) to give (5'). Yield: 7.66 g (89%).

Synthesis of Compound (6'):

The ethyl ester 5' (7.38 g, 17.5 mmol) was dissolved in methanol (35 ml), and to the mixture was added 1 N NaOH (35 ml) dropwise while ice-cooling. After stirring for 2 hours at room temperature, the mixture was poured into a 20% citric acid aqueous solution and extracted with ethyl acetate. The organic layer was washed with water and saturated saline solution, dried with sodium sulfate, and concentrated. This was then dissolved in toluene (50 ml) and heated on an oil bath to 90° C., and, 6 hours later, toluene was evaporated under reduced pressure. Purification using a silica gel column (AcOEt/Hex=1/2) gave compound (6). Yield: 0.95 g (15.5% from the ethyl ester).

Synthesis of Compound (7'):

The lactone compound (6') (0.95 g, 2.72 mmol) was dissolved in anhydrous THF (20 ml) and cooled to −78° C. and 1.1 N LiHMDS (5.4 ml) was added dropwise. After 30 minutes of stirring at −78° C., 3-bromo-2-methyl-propene (550 µl, 5.45 mmol) was added and stirring was continued at −78° C. for 40 minutes. The reaction was terminated by addition of saturated ammonium chloride aqueous solution and extraction was performed with ethyl acetate. Washing with saturated saline solution, drying with $Na_2SO_4$ and purification using a silica gel column gave 0.29 g of the aimed alkene (7'), with recovery of 0.17 of the starting material. The recovered starting material was subjected to the reaction again under the same equivalence conditions, worked up, purified, and the product was combined with the product obtained by the first reaction. Yield: 0.37 g (34%).

Synthesis of Compound (8'):

The alkene (7') (0.37 g, 0.92 mmol) was dissolved in methanol (10 ml), and 5% Pd-C was added and hydrogen gas introduced to perform catalytic reduction. Four hours later, nitrogen gas was introduced to terminate the reaction. After removal of the catalyst by filtration and then concentration, the residue was dissolved in methanol (20 ml), and to this were added triethylamine (TEA) (256 µl, 1.84 mmol) and $Boc_2O$ (400 mg, 1.84 mmol) in the order, and the mixture was stirred overnight at room temperature. After concentration, purification using a silica gel column (AcOEt/Hex=1/4) gave the aimed compound (8'). Yield: 0.48 g.

Synthesis of Compounds (9'), (10', 1'b, 11', 1'a):

The lactone (8') was saponified with sodium hydroxide in methanol. After precipitated with acid and extracted, this was converted to a silyl ether with alkylsilylchloride, imidazole and DMAP in DMF, and purified using a silica gel column to give carboxylic acid (9'). The carboxylic acid (9') and an amino moiety (dipeptide H-Val-Met-NHBzl) were condensed in DMF solvent using EDC and HOBt. After the reaction, workup including extraction, washing, etc. and purification using a silica gel column gave (10'). The silyl ether (10) was TBAF-treated in THF solvent. After the reaction, concentration and combined purification using a silica gel column and ODS-HPLC gave (1'b: TLVM-2). This was subjected to Swern oxidation in DMSO using sulfur trioxide-pyridine complex and triethylamine. After workup including extraction, removal of byproducts such as sulfuric ester by ODS-HPLC separation gave ketone compound (11'). The ketone (11') was dissolved in methanol and reduced with $NaBH_4$ to give an alcohol. This reducing reaction gave a mixture of (1'a) and (1'b). As they were readily separable by ODS-HPLC, they were purified by HPLC separation, thus giving (1'a: TLVM-2).

By the way, staring with this compound, beginning with removal and replacement of its protecting group with a Z group, or, instead, through replacement of the t-butoxycarbonyl group with a Z group at a proper stage in the course of synthesis, similar flow of reactions and removal of the t-butyl group will give the compound shown below.

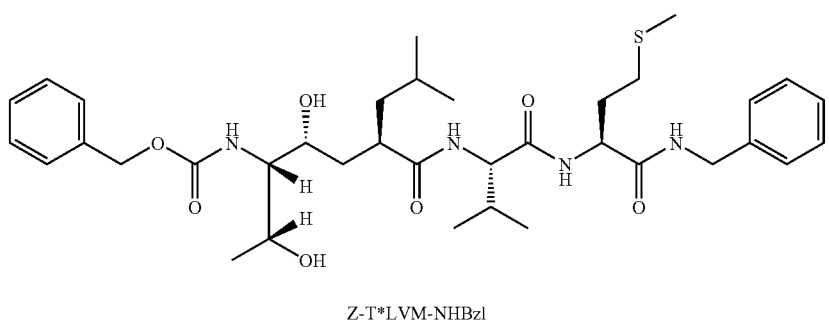

Z-T*LVM-NHBzl

Example 6

Determination of Inhibitory Activity-3

The compounds (1'a) and (1'b) obtained above were measured for inhibitory activity by the same method as in Example 3. As the system for evaluation, however, IMR32, a neural system cell line of human origin, was used after introducing to it a human APP695 gene into which the Sweden mutation had been incorporated.

TABLE 5

|  |  | Aβ40 (pg/ml) | Inhibition rate (%) |
|---|---|---|---|
| Compound 1'a | 100 µM | 0 | 100 |
|  | 10 µM | 31 | 73 |
| Compound 1'b | 100 µM | 26 | 78 |
|  | 10 µM | 72 | 38 |

INDUSTRIAL APPLICABILITY

The present invention provides novel peptidomimetic compounds relating to the pathology of Alzheimer's disease and related diseases thereto. Provision of novel pharmaceutical compositions, as well as means for diagnosis that utilize the characteristics of the compounds, is useful in the clinical and medical field of diseases to which the present compounds relate, in particular, Alzheimer's disease and related diseases thereto.

The invention claimed is:

1. A compound consisting of the amino acid sequence Leu-Val-Met-Leu (SEQ ID NO:3), wherein, between the Leu at position 1 and the Val at position 2, the peptide bond, —CO—NH—, is replaced with a hydroxyethylene group, —CHOH—CH$_2$—, while any other inter amino-acid bond is a peptide bond, wherein the N terminus has an alkyloxycarbonyl group based on C1-10 alkyl that may carry phenyl or naphthyl as a substituent group, wherein the C terminus is converted to an alkyl ester or alkyl amide based on C1-10 alkyl that may carry phenyl or naphthyl as a substituent group, or a pharmaceutically acceptable salt thereof.

2. A composition, comprising the compound of claim 1 or a pharmaceutically acceptable salt thereof and a pharmaceutically acceptable carrier.

* * * * *